(12) United States Patent
Krebs et al.

(10) Patent No.: US 6,365,089 B1
(45) Date of Patent: Apr. 2, 2002

(54) METHOD FOR CROSSLINKING UHMWPE IN AN ORTHOPAEDIC IMPLANT

(75) Inventors: Steven L. Krebs, Arlington, TX (US); Dirk L. Pletcher, Walkerton, IN (US); Ray Gsell, Winona Lake, IN (US); Dale F. Swarts; Gregory S. Meadows, both of Warsaw, IN (US); Gregory K. Taylor, Barberton, OH (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 09/407,220

(22) Filed: Sep. 24, 1999

(51) Int. Cl.$^7$ .............................. A61F 2/32; A61F 2/28; B29C 35/08; B29C 43/02; B29C 43/52
(52) U.S. Cl. ...................... 264/485; 264/85; 264/320; 264/322
(58) Field of Search ...................... 264/85, 320, 322, 264/485

(56) References Cited

U.S. PATENT DOCUMENTS

| | | |
|---|---|---|
| 3,297,641 A | 1/1967 | Werber et al. |
| 3,352,818 A | 11/1967 | Meyer et al. |
| 3,758,273 A | 9/1973 | Johnston et al. |
| 5,037,928 A | 8/1991 | Li et al. |
| 5,160,464 A | 11/1992 | Ward et al. |
| 5,414,049 A | 5/1995 | Sun et al. |
| 5,449,745 A | 9/1995 | Sun et al. |
| 5,466,530 A | 11/1995 | England et al. |
| 5,543,471 A | 8/1996 | Sun et al. |
| 5,879,400 A | 3/1999 | Merrill et al. |
| 6,165,220 A * | 12/2000 | McKellop et al. ........ 623/22.21 |

FOREIGN PATENT DOCUMENTS

| | | |
|---|---|---|
| EP | 0722973 A1 | 7/1986 |
| WO | WO98/01085 | 1/1998 |

OTHER PUBLICATIONS

*Super Low Wear Cross–Linked UHMWPE by Heavy High–Dose Gamma Radiation*Oonishi, H., Kuno, M., Idada, Y., Fujisawa, A., and Masuda, S. 1996 WPOA 2$^{nd}$ Congress of Hip Section.

*Journal of Polymer Science, Part B, Polymer Letters, "The Influence of the Temperature of Irradiation on the formation of Polymer Networks"* D. T. Turner vol. 1, No. 2, Feb. 1963, p. 101.

*The Improvement of Polyethylene Protheses Through Radiation Crosslinking*T.A. du Plessis, C. J. Grobbelaar, and F. Marais Radiat. Phys. Chem. 1977, vol. 9, pp. 647–652.

*The Friction and Wear Behavior of Irradiated Very High Lecular Weight Polyethylene*C. Shen and J.H. Dumbleton Wear 30, (1974) pp. 349–364.

*Crystalline and Supermolecular Structures in Linear Polyethylene Irradiated with Fast Electrons*G. Gielenz and B. J. Jungnickel Colloid & Polymer Science 260, pp. 742–753 (1982).

*Improved Mechanical Behaviour in Ultra–High Modulus Polyethylenes by Controlled Cross–Linking*D. W. Woods, W. K. Busfield and I.M. Ward Plastics and Rubber Processing and Applications 5 (1985) pp. 157–164.

*Irradiation of Ultrahigh–Molecular–Weight Polyethylene*A. Shinde and R. Salovey Journal of Polymer Science: Polymer Physics Edition, vol. 23, 1681–1689 (1985).

(List continued on next page.)

Primary Examiner—Leo B. Tentoni
(74) Attorney, Agent, or Firm—Jacque Wilson

(57) ABSTRACT

A method of manufacturing a bearing for use in an orthopaedic implant, comprises the steps of: providing a radiation source; positioning a bearing material at a distance away from the radiation source; installing a shield over at least a portion of the bearing material; irradiating the bearing material through the shield using the radiation source; and forming a bearing surface on the bearing material.

37 Claims, 22 Drawing Sheets

OTHER PUBLICATIONS

*Ionizing Irradiation for Sterilization and Modification of High Molecular Weight Polyethylenes* Robert M. Streicher Plastics and Rubber Processing and Applications vol. 10, (1988) No. 4, pp. 221–229.

*Influence of Ionizing Irradiation in Air and Nitrogen for Sterilization of Surgical Grade Polyethylene for Implants* R. M. Streicher Radiat. Phys. Chem, vol. 31, Nos 4–6, pp. 693–698, 1988.

*Improvement of Polyethylene by Irradiation in Artificial Joints* H. Oonishi, Y. Takayama, and E. Tsuri Radiat. Phys. Chem. vol. 39, No. 6, pp. 495–504, 1992.

*The Radiation Chemistry of Polyethylene. IX. Temperature Coefficient of Cross–Linking and Other Effects* H. Y. Kang, O. Saito, and M. Dole Journal of the American Chemical Society, 89:9, Apr. 26, 1967, pp. 1980–1986.

*The Radiation Improvement of Polyethylene Prostheses, A Preliminary Study* C. J. Grobbelaar, T. A. Du Plessis, F. Marais The Journal of Bone and Joint Surgery, vol. 60–B, No. 3, Aug. 1978, pp. 370–374.

*Crystalline and Supermolecular Structures in Linear Polyethylene Irradiated with Fast Electrons* G. Gielenz and B. J. Jungnickel Colloid & Polymer Science 260 pp. 742–753 (1982).

*The Effects of Radiation Sterilization on the Properties of Ultrahigh Molecular Weight Polyethylene* H. J. Nusbaum and R. M. Rose Journal of Biomedical Materials Research, vol. 13, pp. 557–576 (1979).

*Radiation Sterilization and the Wear Rate of Polyethylene* R. M. Rose, E. V. Goldfarb, E. Ellis, and A. N. Crugnola Journal of Orthopadedic Research, pp. 393–400, 1984 Orthopaedic Research Society.

*Cross–Linking of Ultra–High Molecular Weight Polyethylene in the melt by means of Electron Beam Irradiation* D. J. Dijkstra, W. Hoogsteen, and A. J. Pennings Polymer, 1989, vol. 30, May, pp. 866–873.

*Improvement of Polyethylene by Irradiation in Artificial Joints* H. Oonishi, Y. Takayama, and E. Tsuji, Radiat. Phys. Chem. vol 39, No. 6, pp. 495–504 1992.

*Effect of $\gamma$ Irradiation on the Fricition and Wear of Ultrahigh Molecular Weight Polyethylene* William R. Jones, Jr., and William F. Hady, Wear, 70 (1981) 77–92.

*Unified Wear Model For Highly Crosslinked Ultra–High Molecular Weight Polyethylenes (UHMWPE)* Orhun K. Muratoglu, Charles R. Bragdon, Daniel O. O'Connor, Murali Jasty, William H. Harris, Rizwan Gul, Fred McGarry 1999 Elsevier Science Ltd.—Biomaterials 20 (1999), pp. 1463–1470.

\* cited by examiner

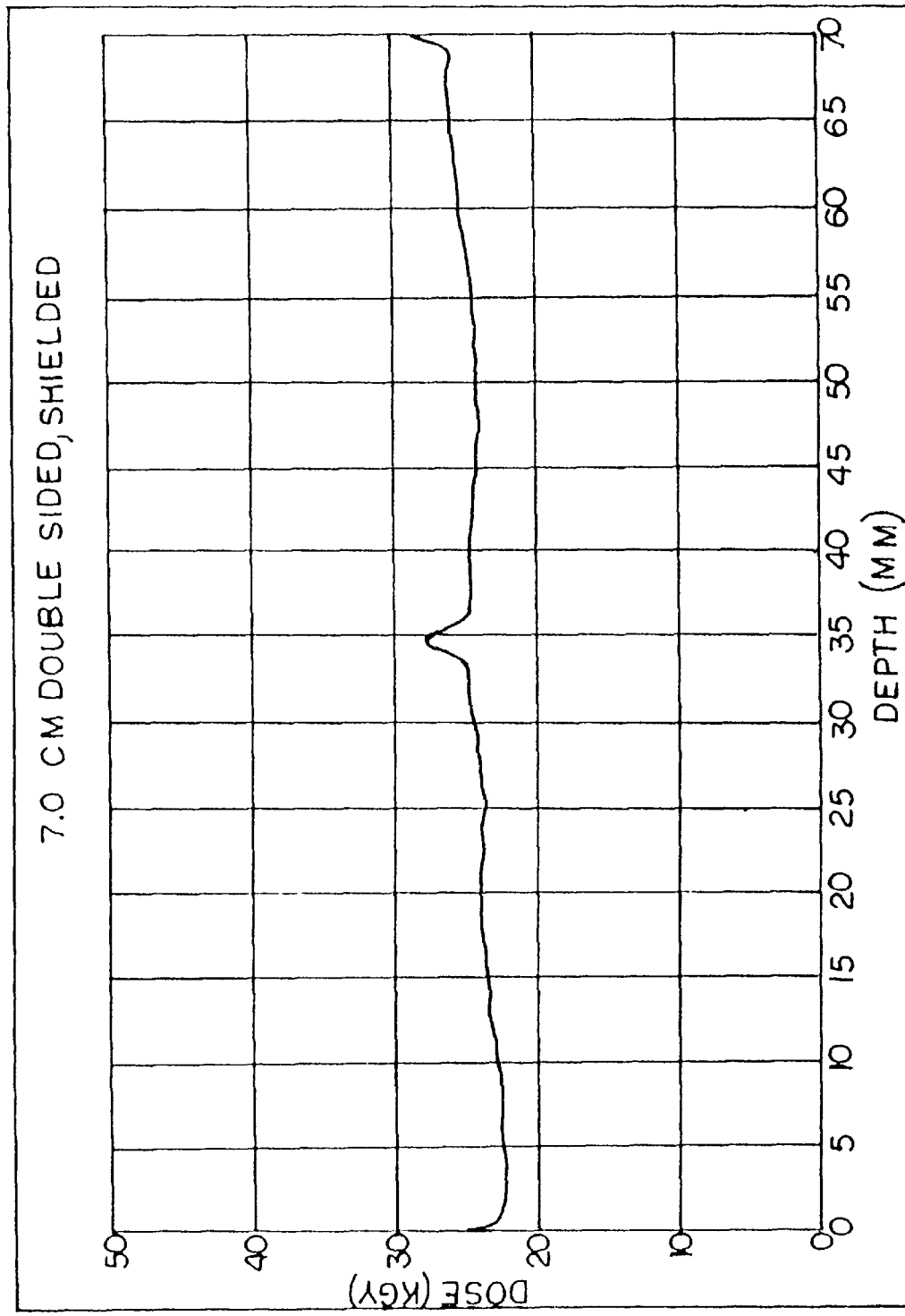

METHOD FOR CROSSLINKING UHMWPE IN AN ORTHOPAEDIC IMPLANT

BACKGROUND OF THE INVENTION

1. Field of the Invention

The present invention relates to methods for enhancing the mechanical properties of polymers such as ultra-high molecular weight polyethylene (UHMWPE). More particularly, the present invention relates to a method for crosslinking UHMWPE to increase its wear resistance in orthopaedic bearing applications.

2. Description of the Related Art

UHMWPE is commonly used as a bearing material paired with an opposing metal component in orthopaedic implants such as hips and knees. It is the high molecular weight of the polymer that imparts the desirable characteristics for implants, such as high impact strength and abrasion resistance. It is known that irradiating certain polymers such as UHMWPE can cause changes in its chemical and mechanical properties. For example when UHMWPE is subjected to gamma irradiation in the range of 3.0–5.0 Mrads, it has been observed that with time it can change color and become embrittled. This is of interest in the medical device field since such an irradiation dose is within the range of commonly used sterilization processes. The general belief is that the changes in material properties are due to competing reaction pathways, one being crosslinking within and between polymer chains, and another being oxidation. Crosslinking results in an increase in molecular weight of the polymer, while oxidation results in decreasing molecular weight. High energy, ionizing radiation, such as gamma or electron beam radiation, breaks molecular bonds, called chain scission, and creates free radicals that are highly reactive species. The severed chains can recombine, crosslink with adjacent chains, or combine with other species such as oxygen. In the presence of oxygen, the severed chain is more likely to form an oxygenated species which is then not able to form crosslinks or recombine, resulting in a reduction of molecular weight. It is the reduction of molecular weight that causes a reduction in mechanical properties and embrittlement. Some of the free radicals formed are not capable of reacting due to location in the polymer structure and thus can exist in the polymer for long periods. The migration of such species as oxygen over long periods of time to these isolated free radicals can result in further oxidation and molecular weight reduction, with a subsequent time dependent degradation of properties.

Crosslinking is known to increase the abrasion resistance of polymers. In orthopaedics it has been indicated as one way to increase the wear life of UHMWPE implants. Crosslinking occurs in polymers when adjacent polymer chains form c—c bonds. Such crosslinking acts to prevent the polymer chains from being pulled or pushed apart. The degree of crosslinking of a material is a function of the radiation dose it receives. The total dose received depends on the penetrative properties of the radiation in the material being treated and the exposure time to the radiation source. State of the art electron beam radiation sources are capable of relatively high dose rates. Thus, relatively short exposure times can yield relatively high doses. Because of this, electron beam radiation facilities typically position a radiation source directed at a moving conveyor on which samples are moved under the electron beam source at a speed selected to give the desired dose. The high dose rates of electron beam irradiation is believed to result in less oxidation than slower irradiation sources such as gamma irradiation, due to the increased availability of oxygen over the longer exposure time of low dose rate irradiation sources.

Some investigators have proposed ways to reduce oxidation and/or increase crosslinking. Their methods generally involve maintaining the article being irradiated in an oxygen free environment. For example, Shen and Dumbleton teach that gamma irradiation in an argon atmosphere results in a high percentage of crosslinking and improves the wear performance of polyethylene. C. Shen and J. H. Dumbleton, *The Friction and Wear Behavior of Irradiated Very High Molecular Weigh Polyethylene*, 30 Wear, 349 (1974). Grobbelaar et al. teach that by gamma irradiating polyethylene prostheses in a reactive organic atmosphere containing acetylene, enhanced crosslinking at the surface is achieved which results in reduced deformation while maintaining excellent abrasion resistance. Grobbelaar et al., *The Radiation Improvement of Polyethylene Prostheses: A Preliminary Study*, 60-B:3 JBJS 370 (1978).

Other investigators have taught free radical elimination via post irradiation processing. Kang et al. teach that crosslinking polyethylene with gamma irradiation is enhanced by raising the temperature of the polyethylene during irradiation and furthermore that free radicals can be removed by annealing the polyethylene after irradiation. Kang et al., *The Radiation Chemistry of Polyethylene. IX Temperature Coefficient of Cross-Linking and Other Effects*, 89:9 Journal of American Chemical Society 1980 (1967). Sun et al. likewise teach in U.S. Pat. No. 5,414,049 that free radicals may be removed by heating the irradiated article.

In addition to dealing with free radicals, problems may arise when irradiating thick parts with high dose rates. Early investigators used low dose rate gamma irradiation that easily penetrated through parts of various thicknesses and achieved desired dose levels over many hours of exposure to the gamma source. The present investigators have found it advantageous to use E-beam irradiation because of its very high dose rate and capability of reaching desired dose levels very quickly. However, orthopaedic applications may require parts up to 9 cm to be treated. A problem with irradiating parts over 4 cm with an electron beam is that an electrical charge potential can build up within the material being irradiated, and then discharge, leading to defects characterized by carbon tracking or scoring. This carbon tracking or scoring may be visible with the naked eye or only with the aid of magnification. The carbon scoring appears as black "lightning strikes" in the polymer mass or as black marks on the polymer surface. Another problem that arises is that the energy level of the irradiation source determines the depth to which the irradiation will penetrate. With sources in the 10 MeV range, which is typical for commercial E-beam vendors, penetration occurs at approximately 4.0–5.5 cm. Furthermore, the dose delivered to the sample over this penetration depth is not uniform.

SUMMARY OF THE INVENTION

The present invention provides a method for irradiating polymers such as UHMWPE to produce property enhancing crosslinking. The method is particularly advantageous in that it can rapidly process parts of varying thickness while producing a desired dose distribution through the sample thickness. Likewise the method can process thick parts with minimal electrical discharge. Finally, the method includes steps to reduce or eliminate free radicals from the irradiated UHMWPE.

These advantages are achieved by a method which includes determining the desired dose distribution in the sample to be irradiated, determining the optimal thickness to produce the desired distribution with a particular electron source, determining whether a shield or shields will be necessary in combination with the sample to replicate the optimum thickness, and assembling the sample and shields and irradiating the assembly on one or more sides. In addition a variety of electrical discharge control methods and devices are disclosed.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIGS. 26–28 are graphs of resultant dose for two-sided irradiation of different thickness shielded samples of the type shown in FIG. 19.

Corresponding reference characters indicate corresponding parts throughout the several views.

DETAILED DESCRIPTION OF THE INVENTION

The following description describes the theories, research, findings, and applications of applicants invention by the way of illustrative examples. Applicants invention should not be considered to be narrowly limited to the particular examples used.

Electron beam irradiation of UHMWPE will vary in the depth of penetration depending on the energy level of the accelerated beam. The greater the energy level, the greater the depth of penetration. Useful energy levels for the present invention can range from 1 to 20 MeV at a beam power of from 1 to 120 kW. Typical commercial electron beam sources use a 10 MeV beam at a beam power of 60 kW. An electron beam of 10 MeV and 60 kW beam power will penetrate UHMWPE to a depth of approximately 4 to 5.5 cm.

Figure 1:
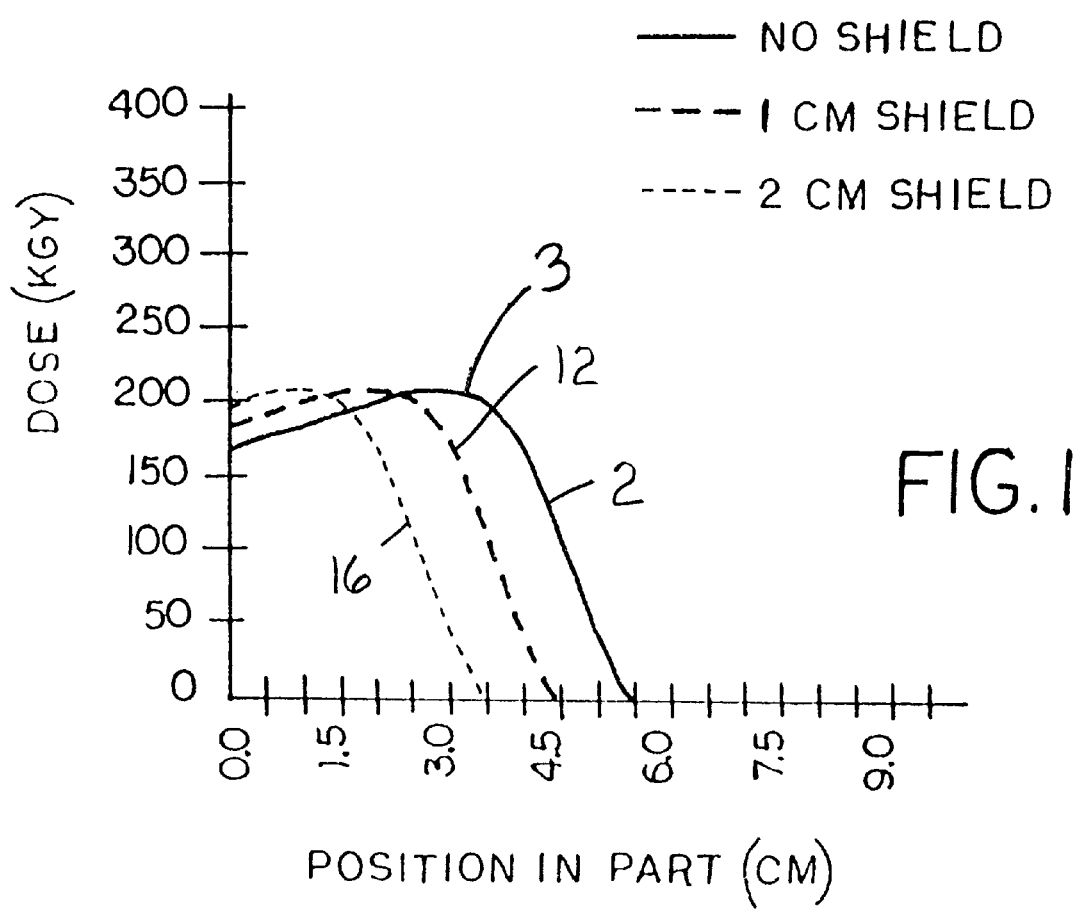
FIGS. 1–3 are graphs illustrating dose curves of a shielded and unshielded polymer sample.
Figure 2:
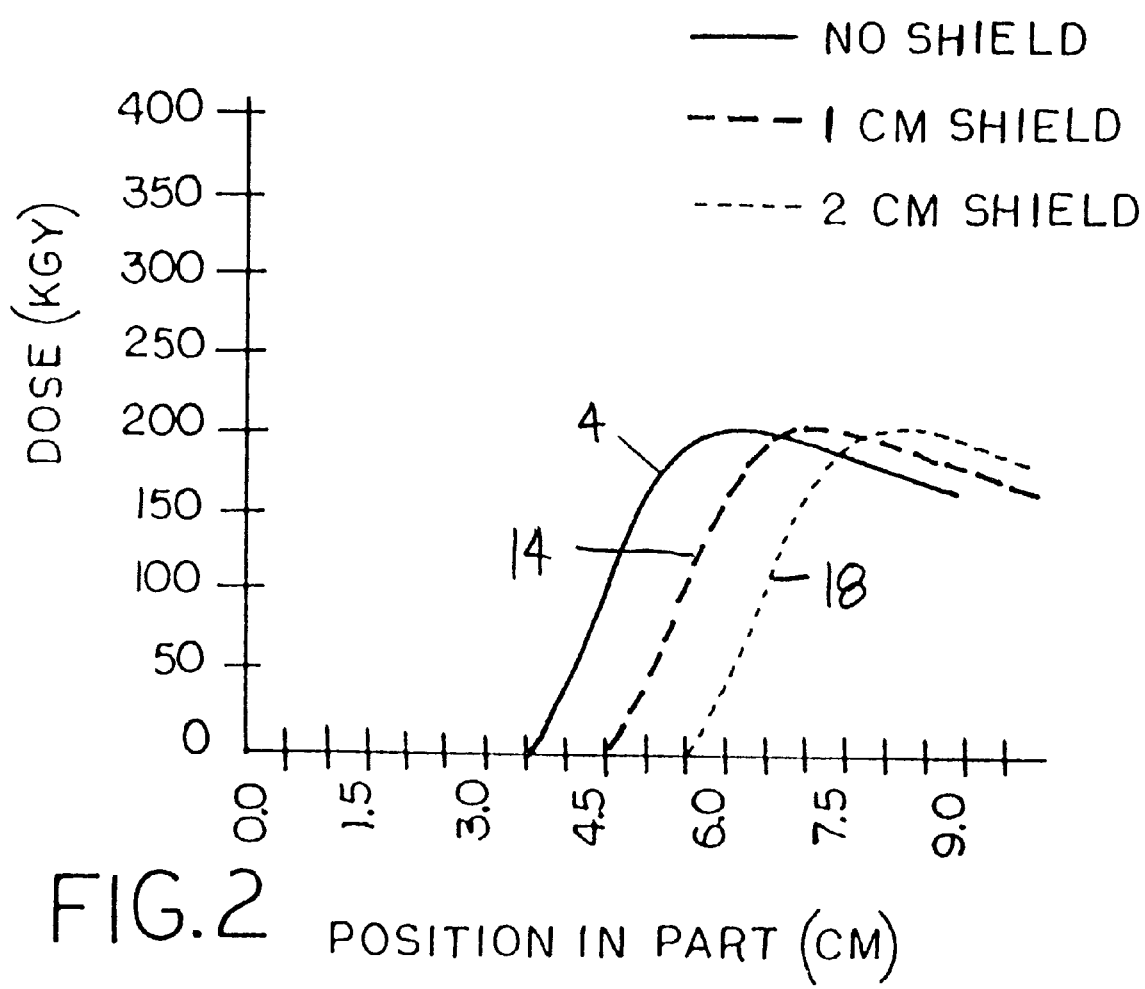
Figure 3:
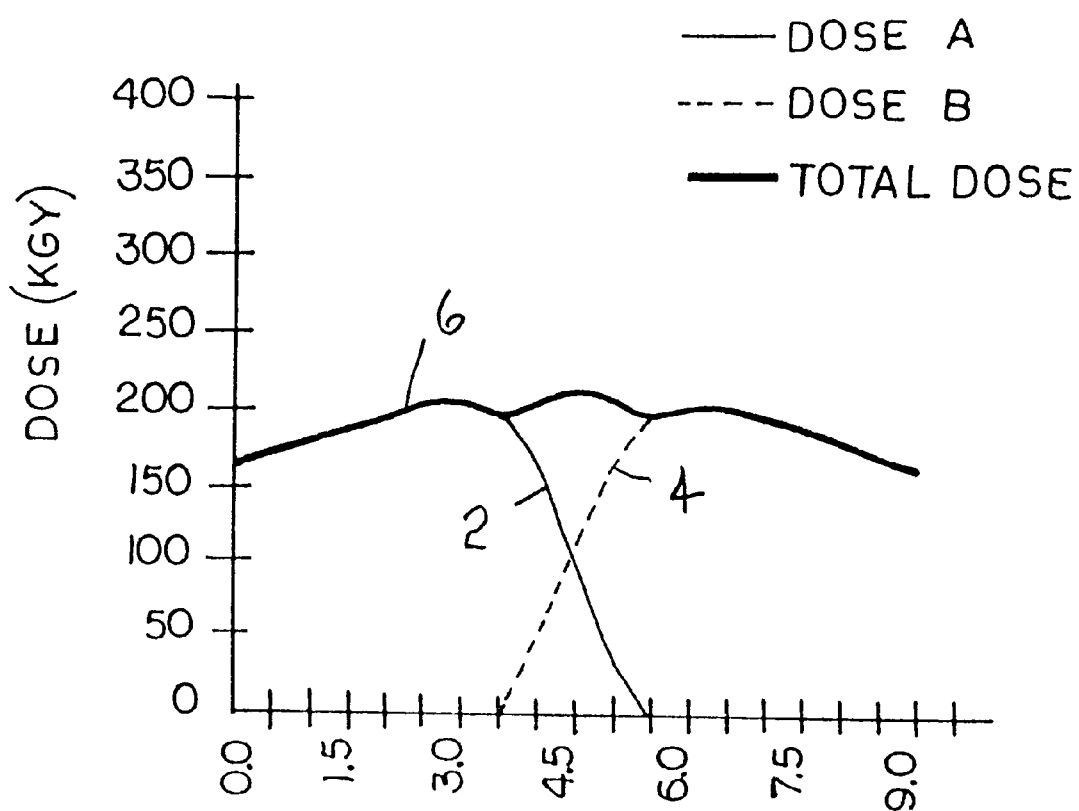
Figure 4:
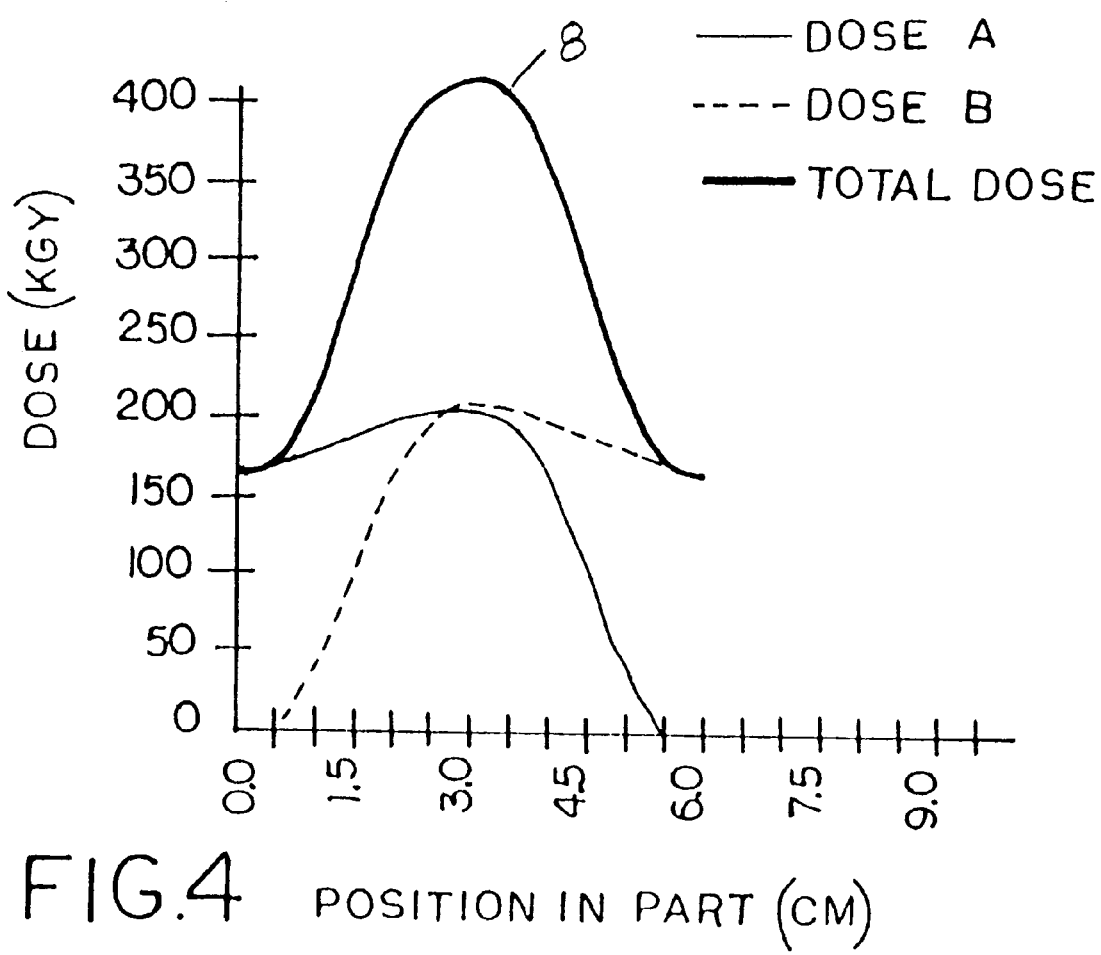
FIG. 4 is a graph illustrating a dose curve for a sample having a less than optimal thickness.
Figure 5:
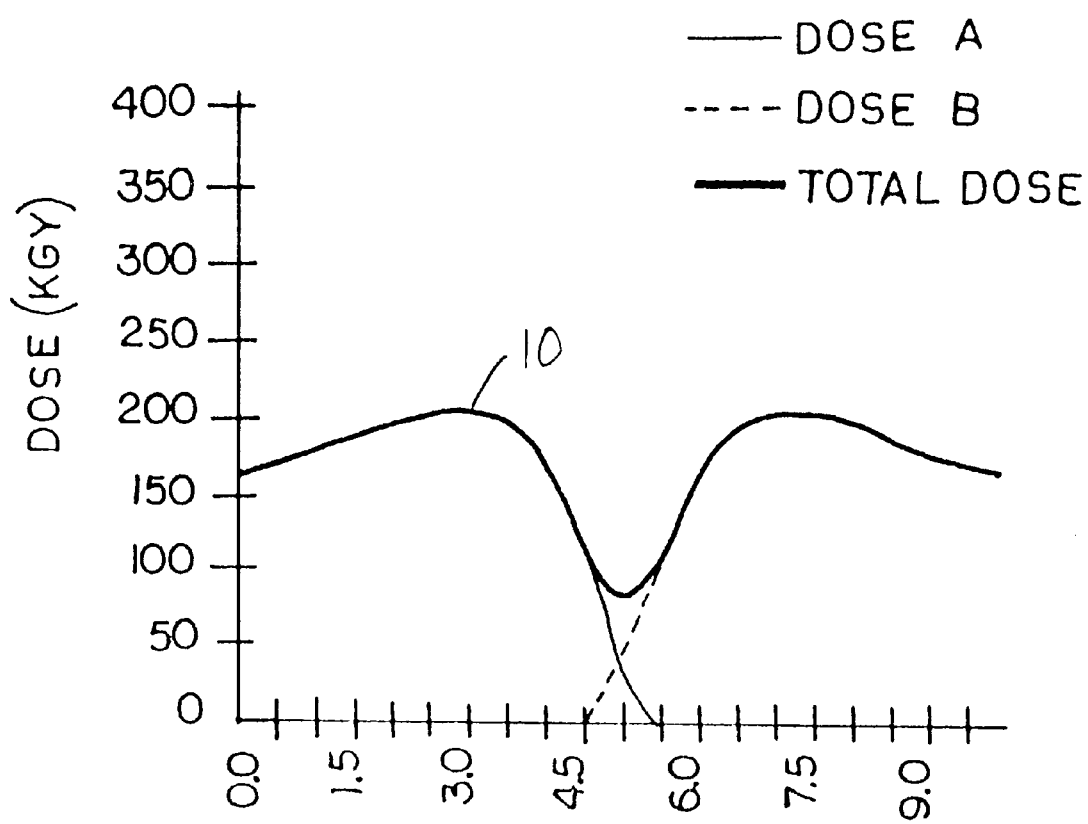
FIG. 5 is a graph illustrating a dose curve for a sample having a greater than optimal thickness.

FIG. 1 shows a theoretical dose curve 2 for a 10 MeV beam depicting how the dose received by a 9 cm UHMWPE sample varies with position in the sample. The top of the sample is at position 0 cm and the bottom is at 9 cm. Note the subsurface dose peak 3 that occurs with single-side irradiation. This peak is caused by the cascade effect wherein the energy level of the incident electron beam is sufficient to eject electrons from the target material. The ejected electrons have sufficient kinetic energy to break molecular bonds, thus adding to the incident dose. This process repeats itself until the kinetic energy of the incident and ejected electrons have been reduced due to inelastic collisions, resulting in diminishing penetration through the material. In order to irradiate all of a 9 cm thick sample, the sample must be turned and irradiated again on the opposite face. FIG. 2 shows the dose curve 4 produced by irradiating the bottom of the sample. FIG. 3 shows the total dose 6 throughout the part when the doses from top and bottom side irradiation are combined. As can be seen, for any particular energy level, there will be a sample thickness for which irradiation of the top and the bottom will result in a substantially uniform dose 6 across the part thickness as shown in FIG. 3. For parts having thicknesses different from this, the dose will be non-uniform. For instance, in the present example, if a 6 cm sample is irradiated from both sides under the same conditions, a substantial dose overlap will occur yielding a much higher dose 8 in the middle of the sample than at the outside of the sample as shown in FIG. 4. Likewise, if a 10 cm sample is irradiated from both sides under the same conditions, less dose overlap will occur yielding a much lower dose 10 in the middle of the sample than at the outside of the sample as shown in FIG. 5. This dose distribution might be desirable where one wants to crosslink near the surface, such as for abrasion resistance, and leave the interior of the sample uncrosslinked to maintain the original material properties. Thus, there is an optimum sample thickness to produce a desired dose distribution for any particular combination of material and electron source energy. By carefully matching electron beam energy level and sample thickness it is possible to produce samples with a substantially uniform dose distribution, with a dose peak in the sample interior, or with a dose minimum in the sample interior to meet the needs of different applications.

Manufacturing efficiency requires flexibility in being able to process materials of different thicknesses and with different dose distributions. However, it is often the case that cost considerations require the use of an electron beam source with a fixed energy level. The advantageous tailoring of dose distribution described above, as well as other dose control, can be achieved with a fixed energy level source by using shields between the electron source and the sample being treated. The penetration of electron beam irradiation into a sample is a function of the density of the material through which the beam must pass. Therefore, so long as one knows the optimum sample thickness to achieve the desired dose distribution from the available electron source, one can use shields with samples thinner than the optimum to achieve the same dose distribution. For example, FIGS. 1 and 2 show how placing a shield adjacent the surface at which the radiation is being directed moves the distribution in the direction of the shield. In FIGS. 1 and 2, a shield having the same density as the sample is used. Thus, 1 cm and 2 cm shields result in dose distributions, 12, 14 and 16, 18, that are offset by 1 cm and 2 cm, respectively. The shields need not be of the same material as the sample. To calculate the appropriate shield thickness for any sample/shield combination, the following formula is used:

1. Total Shield Thickness =

$$\frac{(\text{optimum sample thickness} - \text{sample thickness}) \times (\text{sample material density})}{(\text{shield material density})}$$

For example, it is desirable to machine acetabular cups from a block of crosslinked UHMWPE. It is also desirable, to facilitate manufacturing, that the block be crosslinked uniformly so that the block can be machined in any orientation and still have crosslinked material at the bearing surface. To produce a suitable block using the present invention, first determine the block thickness necessary for the part to be made. For uniform crosslinking, the electron source must be selected to have at least enough energy to penetrate from both sides of the block and overlap enough to produce a uniform dose distribution as shown in FIG. 3. If the electron energy level is in excess of that required, shielding can be used. If the electron energy level is deficient then the dose will be lower in the middle of the block and will not produce uniform crosslinking.

Figure 6:
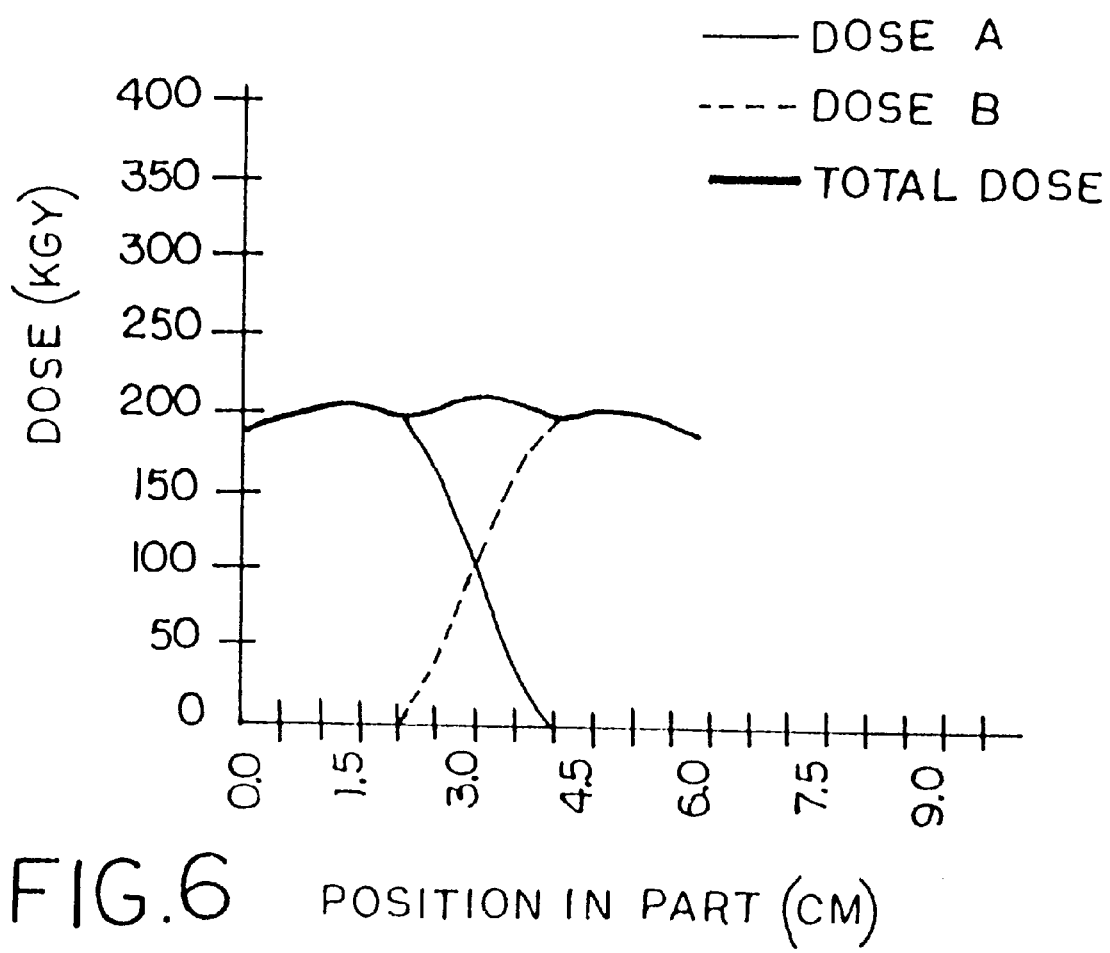
FIG. 6 is a graph illustrating a dose curve for a sample having a shield placed on opposite sides thereof.

It has been found that for a 10 MeV electron source that the optimum thickness for uniform crosslinking for UHMWPE is approximately 9 cm. To uniformly dose a 9 cm thick sample, it is passed under the electron beam, turned over to expose the opposite side, and passed under the beam again. Such a treatment is depicted in FIG. 3. In order to uniformly dose a 6 cm thick sample of UHMWPE, it is first necessary to determine an appropriate shield thickness. For a shield material with the same density as the sample, such as an UHMWPE shield, the densities divide out and the total shield thickness is simply the optimum thickness for uniform crosslinking minus the sample thickness. In this example that would be 9−6=3 cm. In order for the dose distribution to be symmetrically located within the sample, the total shield thickness is divided by two and each side of the sample is shielded by this half-shield thickness when it is irradiated. Thus for this example, each side of the sample would be shielded with a 1.5 cm UHMWPE shield to yield the dose distribution shown in FIG. 6. Alternatively, one side may be irradiated unshielded, following with the opposite side shielded with the calculated thickness from formula 1.

Figure 7:
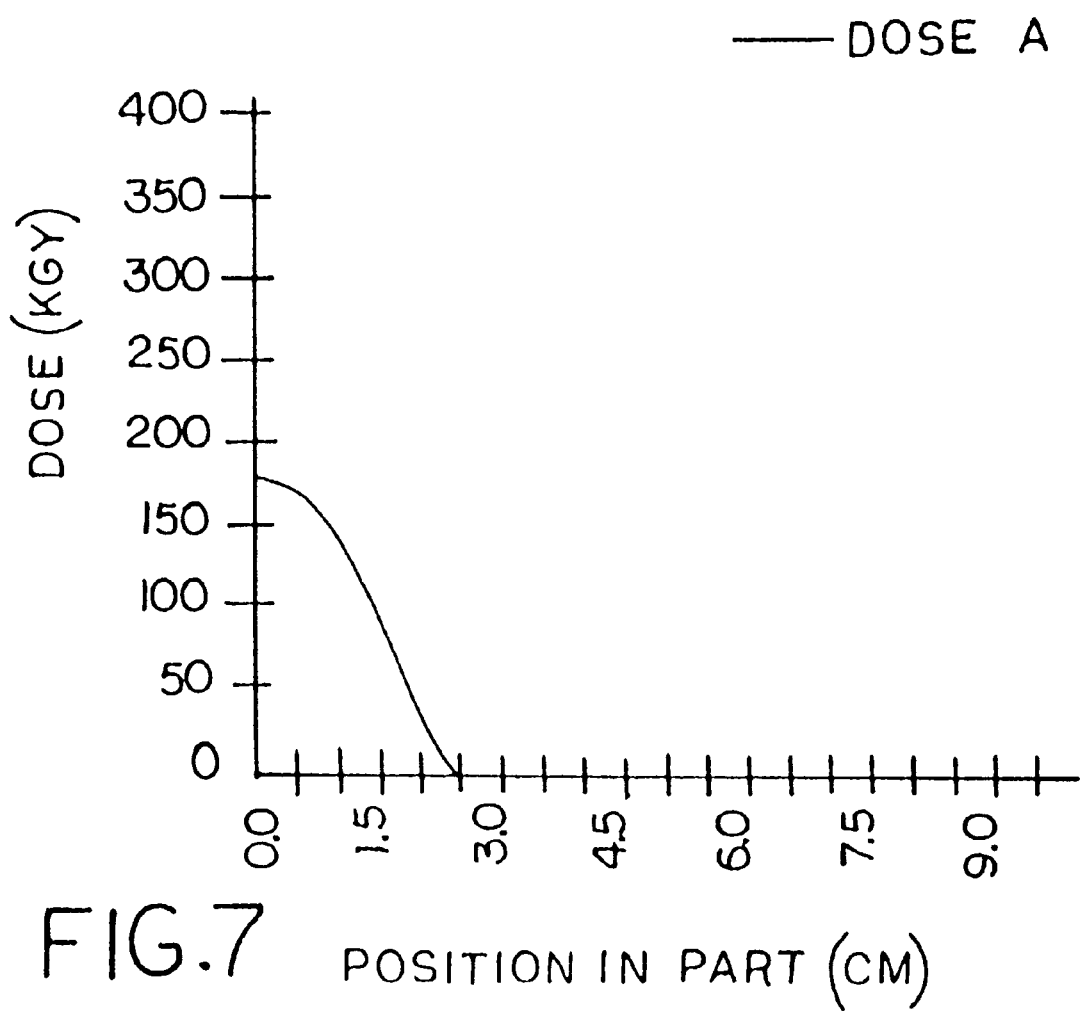
FIG. 7 is a graph illustrating how the dose curve may be shifted utilizing a shield.
Figure 8:
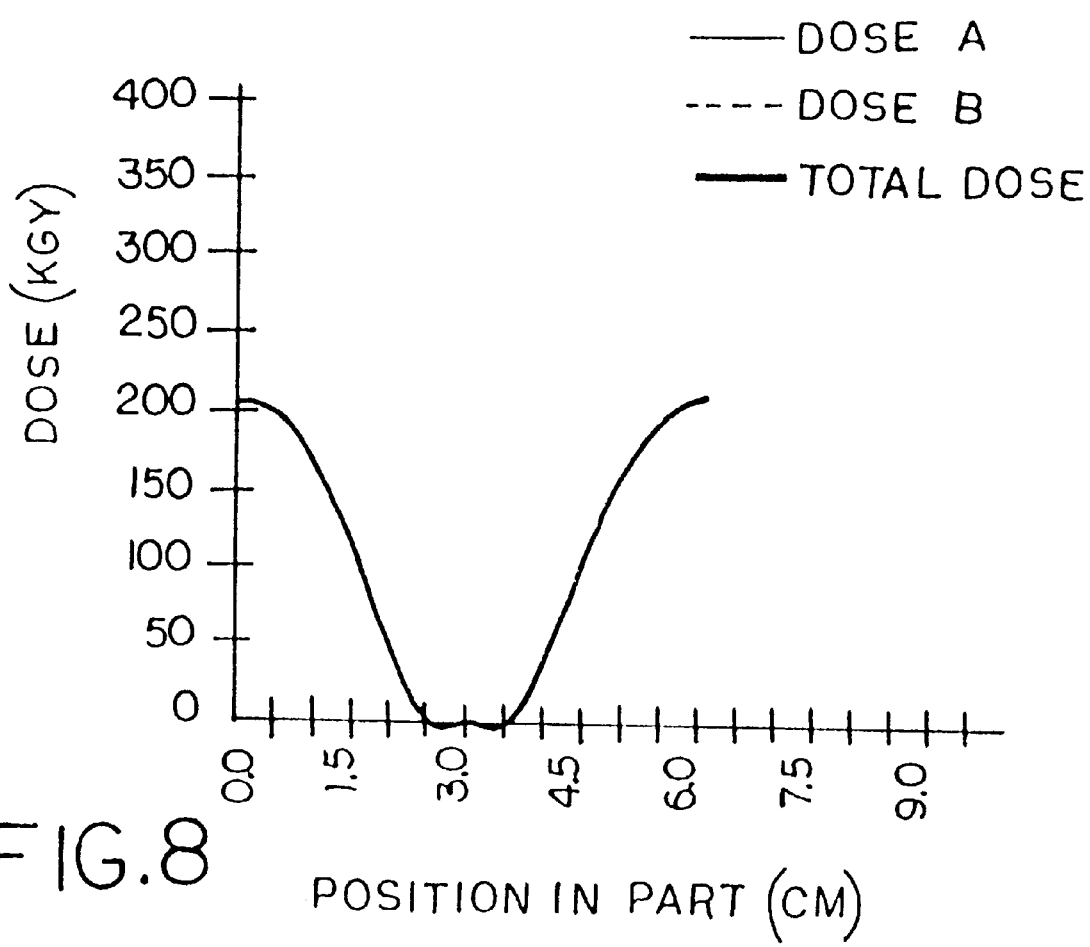
FIG. 8 is a graph illustrating another dose curve which may be obtained using shielding.

There may be applications where a non-uniform dose distribution is desired. For example, it may be desirable to have a higher dose near the articular surface of a finished implant for improved wear properties but a lower dose in the rest of the implant for better mechanical properties. This can be achieved by only irradiating one side and shielding it to move the subsurface peak to the surface of the sample to yield the dose distribution of FIG. 7. In another circumstance it may be useful to have a higher dose at the top and bottom of a sample to improve wear properties at opposite surfaces, for example in a mobile bearing knee or an acetabular cup, and low dose in the middle of the sample to maintain mechanical properties. One way to achieve this is by irradiating a sample thicker than the optimum thickness for a uniform dose as discussed relative to FIG. 5. A more adaptable way is to use shielding. Using the same conditions of our previous examples, a 6 cm UHMWPE sample irradiated from both sides with a 3 cm shield used for both passes has a total shield thickness of 6 cm, an apparent sample thickness of 12 cm and yields the symmetric dose profile of FIG. 8.

Other shield materials may advantageously be used. For example, a more dense material may be used for reasons of reducing bulk and increased durability. Aluminum is a preferable shield material. Using the shield thickness equation for an aluminum shield and a polyethylene sample gives the following shield thickness:

2. Total Shield Thickness = $\frac{(9\,\text{cm} - 6\,\text{cm}) \times (0.936\,\text{g/cm}^3)}{(2.7\,\text{g/cm}^3)} = 1.04\,\text{cm}$ Where 9 cm is the optimum sample thickness for a particular desired dose distribution, 6 cm is the sample size to be treated, 0.936 g/cm$^3$ is the density of UHMWPE and 2.7 g/cm$^3$ is the density of aluminum. As can be seen, this formula allows a shield thickness to be determined for any appropriate material.

Figure 10:
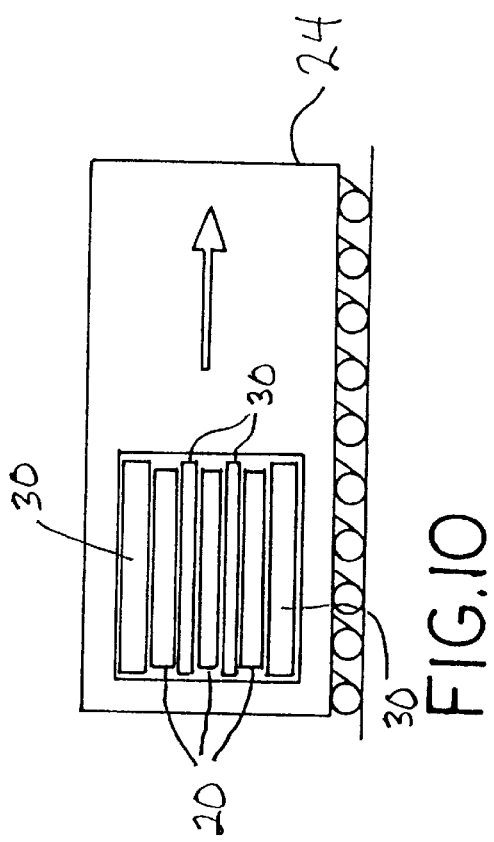
FIGS. 9–11 illustrate an embodiment of an equipment setup used for carrying out an embodiment of the method of the present invention.
Figure 11:
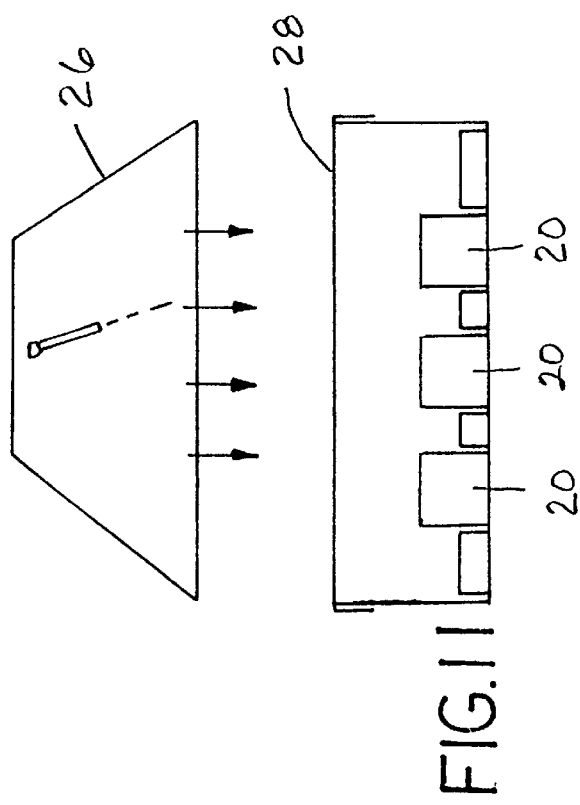
Figure 9:
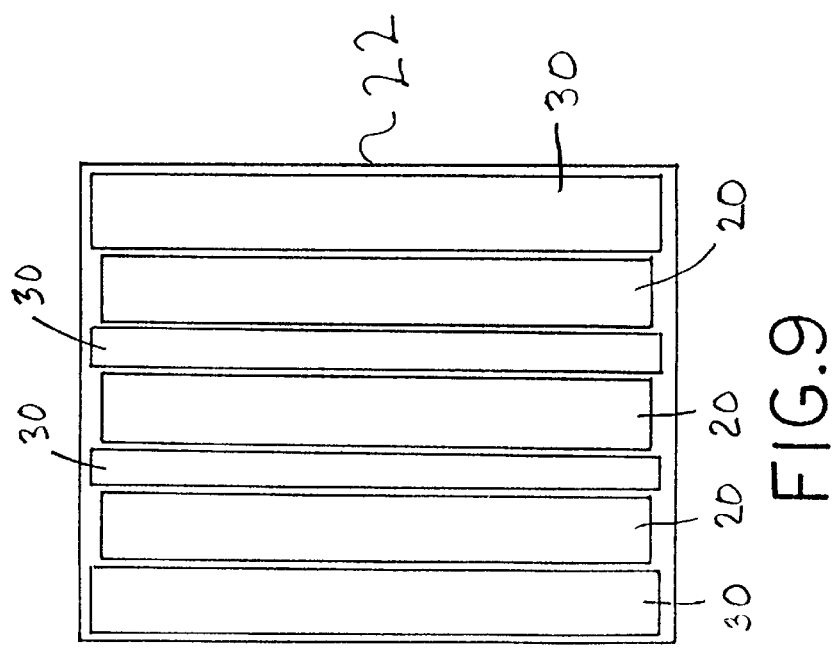

In order to achieve the dose profiles discussed above, the equipment setup of FIGS. 9–11 has been utilized. Samples 20 are placed in a container 22 on a conveyor belt 24. The conveyor moves the samples under an electron beam source 26. It has been found that a total dose of about 100 kGy is useful for reducing wear in laboratory specimens. The dose range useful for imparting crosslinking with a resultant improvement in wear is from 30 to 300 kGy, and more preferably between 50 and 150 kGy, with the most desirable range being between 80 and 120 kGy. A dose of 100 kGy can be achieved by using a 10 MeV electron beam source at 60 kW beam power, a scan-width of 80 cm, a distance from the scan-horn window of approximately 110 cm, and a sample (conveyor) speed of 54.2 cm/min. In the case where a shield is desirable, the shield can simply be laid on top of the samples, or on the pan. If two passes are required with shielding of the top and bottom of the sample 20, then the same shield can be used by removing it from the sample or pan, turning the sample and replacing the shield. Preferably, the shield can be fitted as a cover 28 for the container 22. Alternately, separate shields could be attached to each of the top and bottom of the sample 20. Samples of different cross sectional shapes can be processed according to this invention. Preferably, samples will have flat sides so that the samples can be rested on the flat sides to maintain their orientation relative to the electron source to facilitate careful dose control. Spacers 30 are preferably used to keep the samples 20 from changing position within the container 22 during processing.

Figure 12:
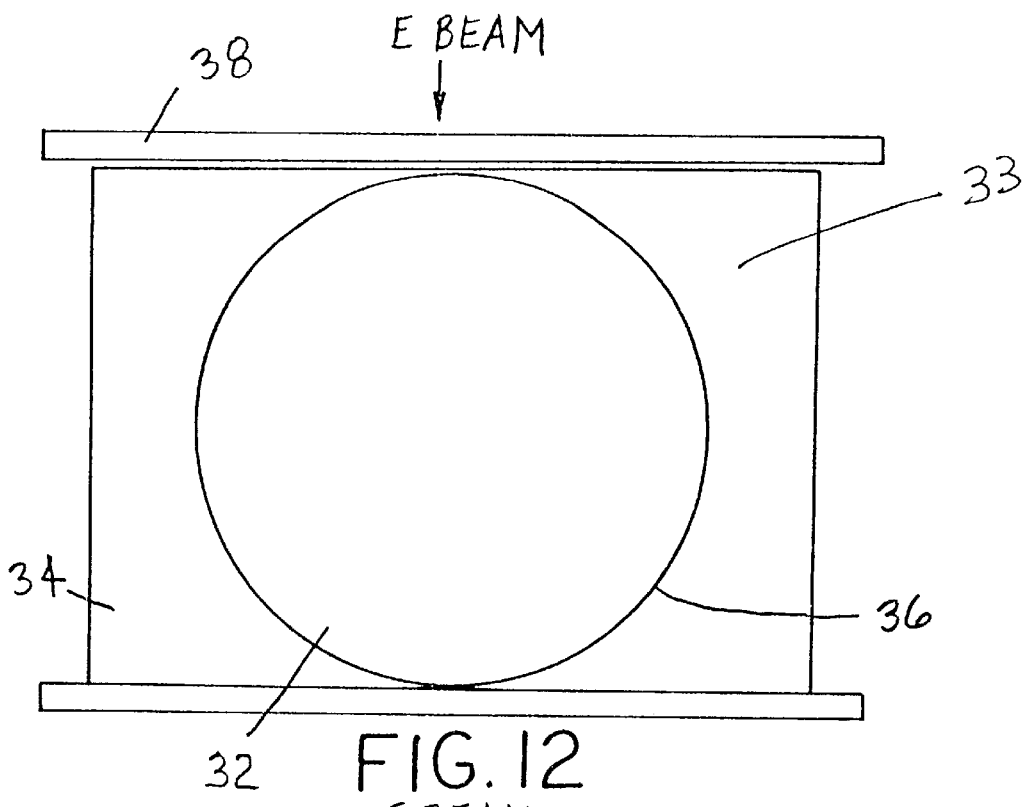
FIG. 12 is an end view of a cylindrical sample carried by a conductive holder.

Samples with non-rectangular cross sections, can also be processed according to this invention. Care must be taken to ensure that the sample is indexed 180 degrees if it is turned for a second pass. FIG. 12 shows a sample with a non-rectangular cross section. In particular, a round bar 32 is inserted into a flat-sided carrier 34 having a cylindrical cavity 36 for receiving the bar 32. The carrier 34 prevents the bar 32 from rolling and facilitates rotating the bar 180 degree for a second pass. A shield 38 is placed on top of the carrier to yield the optimum sample thickness for the particular dose profile desired. In addition to or in place of the shield 38, the carrier 34 can be used as a shield to control the dose received by the bar 32. For example, as shown, a carrier with a rectangular outer profile and an interior sized to closely receive the sample can be made of a material with the same density as the sample. Thus the dose received by the sample/carrier assembly would resemble those of the prior examples. In addition to round bars, other shapes could be carried and/or shielded in this way. For example, extruded bars with the profile of a knee articular surface are currently available. By combining such a bar with a shield shaped to mate with it, dose distributions similar to rectangular bars can be produced.

Figure 13:
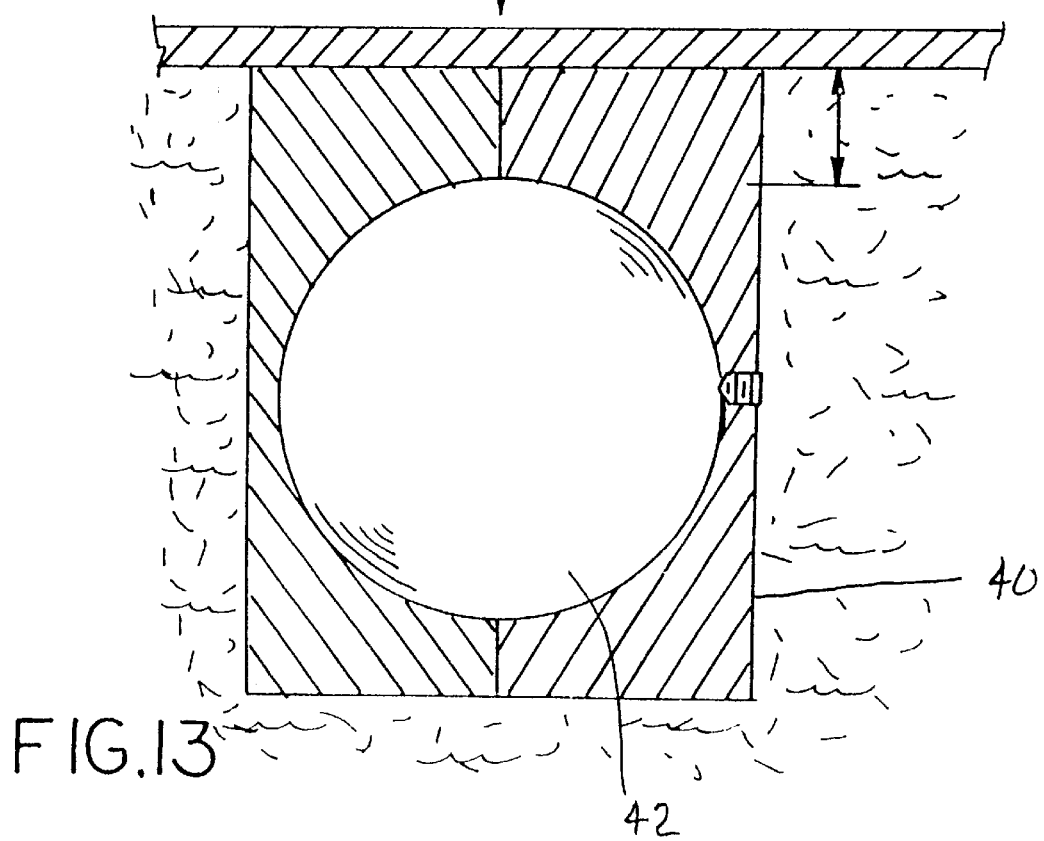
FIGS. 13 and 14 illustrate clamps which may be used to support a sample manufactured in accordance with the method of the present invention.
Figure 14:
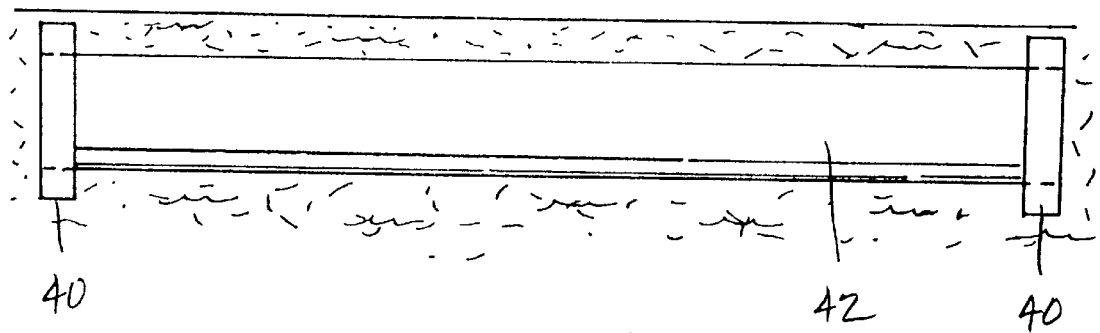

It is also within the scope of this invention to use a carrier for non-rectangular samples with a density different from the sample. As can be seen in FIG. 12, the carrier provides more shielding material in regions 33 away from the centerline of the sample. Thus, a carrier with a density greater than the sample will produce a higher dose in a region extending from the top of the sample down through the center of the sample with a lower dose on the sides of the sample. A carrier with a density less than the sample will produce a lower dose in the region extending from the top of the sample down through the center of the sample with a higher dose on the sides of the sample due to the thickness of the sample near the centerline. This can be carried further as shown in FIGS. 13 and 14 in which end clamps 40 support the bar 42 and there is no carrier along the length of the bar 42. These effects can be used to advantageously locate areas of high and low desired dose. Likewise, shields with varying cross sections, both facing the beam and facing the sample, can be used to tailor the dose profile.

Figure 17:
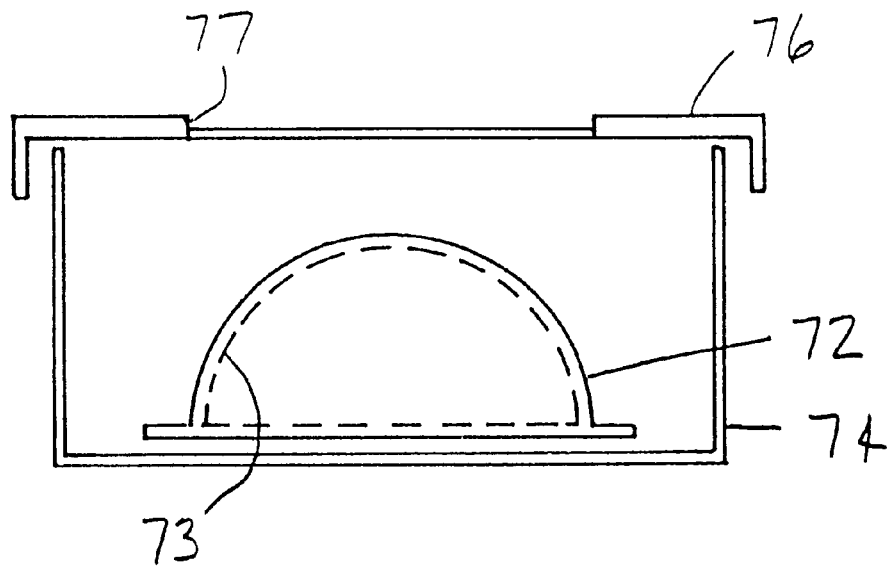
FIG. 17 illustrates another embodiment of a shield of the present invention with a cutout therein.

Both bulk implant bearing material and finished formed bearing material can be crosslinked according to the present invention. Crosslinking of bearing material after it has been formed into an implant would require that the implant be maintained in an inert environment such as nitrogen or argon gas, or a vacuum to prevent oxidation of the implant surface. Selective shielding may be desirable in certain designs or applications. For example, it may be desirable for the articulating surface of an acetabular cup to be highly crosslinked, while maintaining a lower level of crosslinking in the rim area of the cup. This would provide improved wear resistance while maintaining higher mechanical properties and toughness in the rim area where cup location and locking mechanism devices are typically located. This would also provide for improved resistance to damage from hip stem neck impingement. An example of a shielding device to achieve this is depicted in FIG. 17, where an acetabular cup 72 with an articulating bearing surface 73 is held in a fixed position within the metal container 74, and an appropriate shield ring 76 with a cutout 77 covers the rim area of the cup to prevent or lower the radiation dose received by the rim area.

Figure 18:
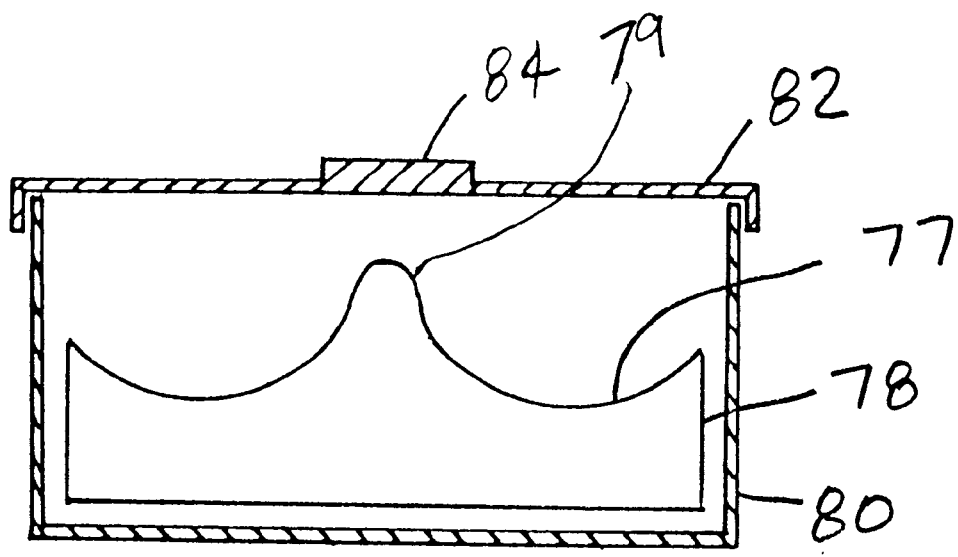
FIG. 18 illustrates another embodiment of a shield of a present invention with a shield of varying thickness.

Similarly, for an UHMWPE knee tibial insert, it may be desirable to restrict the crosslinking to the articulating surfaces while maintaining higher mechanical properties in non-articulating areas of the device. For example, in a posterior stabilized device, the stabilizing post may be subjected to higher mechanical shear force where better mechanical properties are desired over wear resistance. As shown in FIG. 18, the post area 79 could be selectively shielded while allowing the articulating bearing surfaces 77 to be highly crosslinked by placing the tibial insert 78 in a container 80 with a shield 82 having extra shielding 84 over the post area 79.

Figure 15:
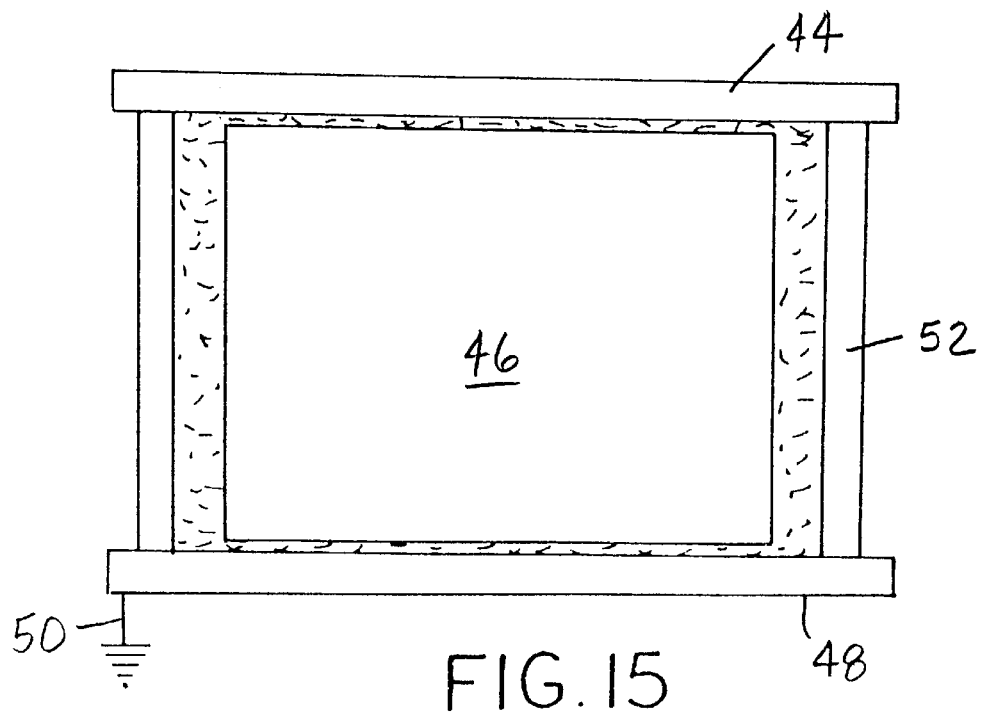
FIG. 15 illustrates a sample placed within a conductive, grounded container.

When irradiating thick samples with a high rate of radiation such as with electron beam irradiation, it has been found that electrical charge can build in the sample in a capacitive manner. When the charge reaches a level to overcome the dielectric strength of the sample, it can discharge through the sample leaving charred paths that spoil the sample for its intended use. FIG. 15 shows one way to dissipate charge before it can build to high levels. A conductive shield 44 is placed over the sample 46 which is placed in a conductive container 48 with a ground 50. By providing a conductive path 52 from the shield 44 to the container 48, charge is dissipated from the sample 46 to the container 48 and on to ground.

Figure 16:
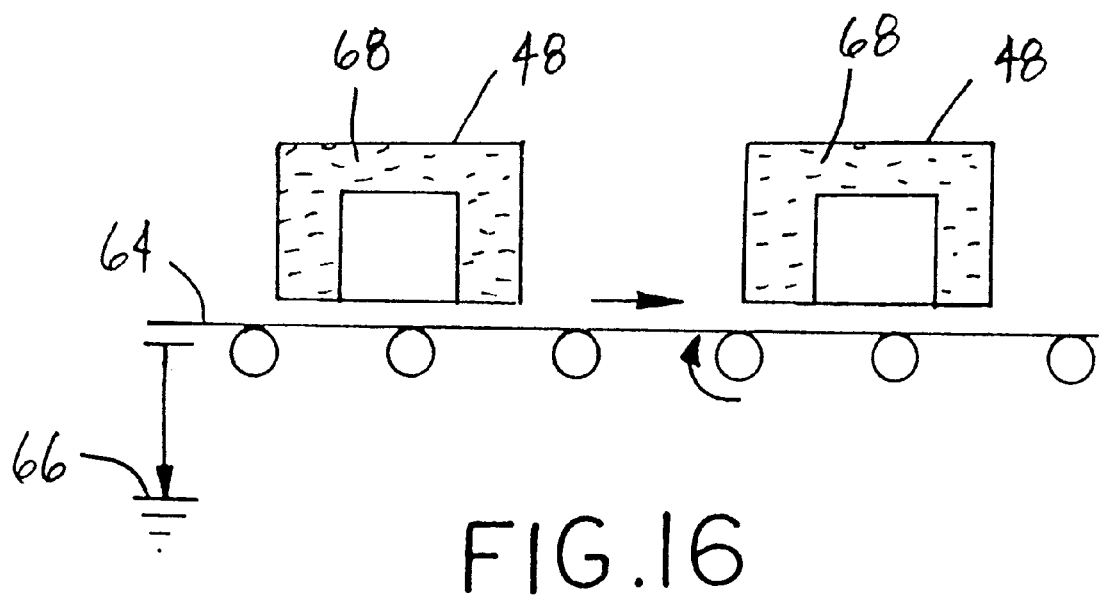
FIG. 16 illustrates the conductive container of FIG. 15 placed on a conveyer.

As shown in FIG. 16, conductive container 48 may be placed on a conductive conveyer 64 which is grounded 66. In addition, the space 68 surrounding the sample may be filled with a conductive media in the form of a fluid or solid to improve dissipation. The conductive medium 68 preferably provides an environment for a controlled rate of electrical charge dissipation from the sample being irradiated. The conductivity of tap water has been found to work effectively. Such a filler is also advantageously used to exclude oxygen from the surface of the sample to reduce oxidation during irradiation. It has also been found that the electrical conductivity of UHMWPE can be increased by maintaining the sample at an elevated temperature so that charge dissipates through the sample at lower, non-destructive levels. Testing has shown that raising the temperature also increases the crosslinking efficiency and reduces wear in pin-on-flat tests. Preheating the sample to between 20 and 60° C., preferably between 40 and 50° C., works well. The rate of dose application has also been found to significantly effect the tendency for electrical discharge. Lower dose rates tend to cause more discharge, and at lower total applied dose. Mass of the item being irradiated also effects the tendency to discharge, with larger mass blocks discharging more readily. Certain thickness' of UHMWPE that could not be evenly irradiated from one side only may tend to discharge severely if irradiated from two sides without shielding, if the center section of the mass becomes overdosed, since this is also where the electron charge tends to collect in the mass. Shielding thus allows these thickness' of material to be irradiated without discharge, and with a uniform dose.

Specific examples for carrying out the method of the present invention will now be described in detail.

Figure 19:
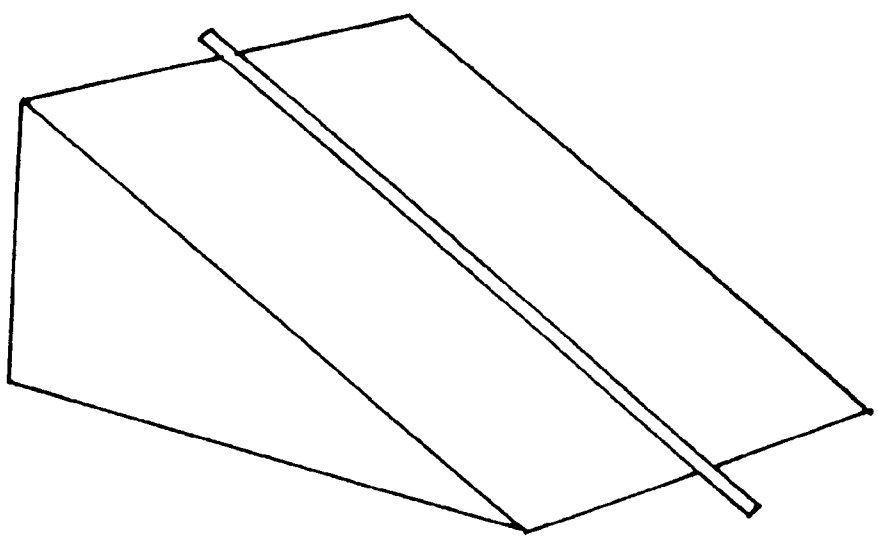
FIG. 19 is a perspective view of one-half of a dose measurement block showing a radiochromic dosimeter film in place on the block.
Figure 20:
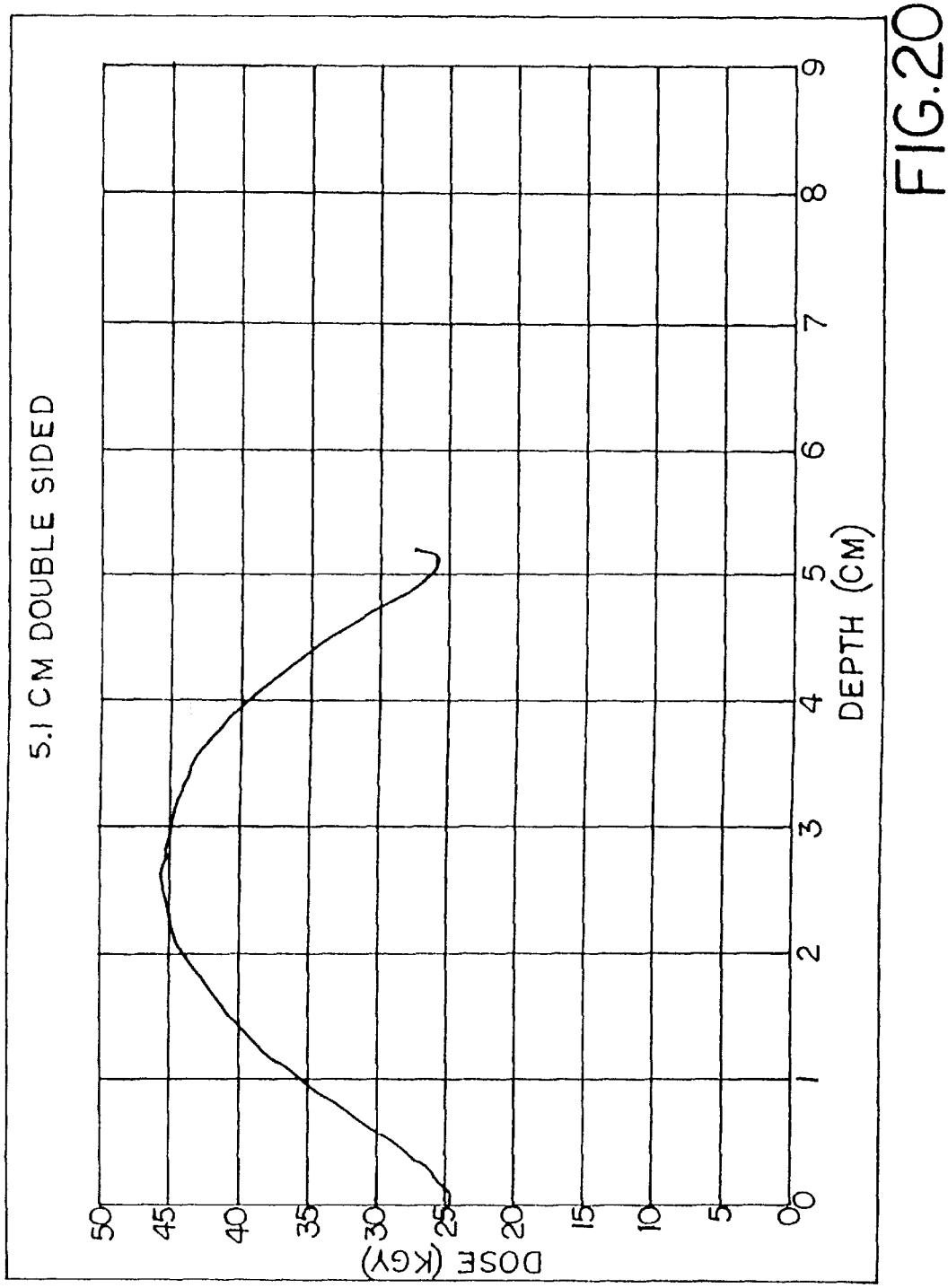
FIGS. 20–24 are graphs of resultant dose for two-sided irradiation of different thickness samples of the type shown in FIG. 19.
Figure 21:
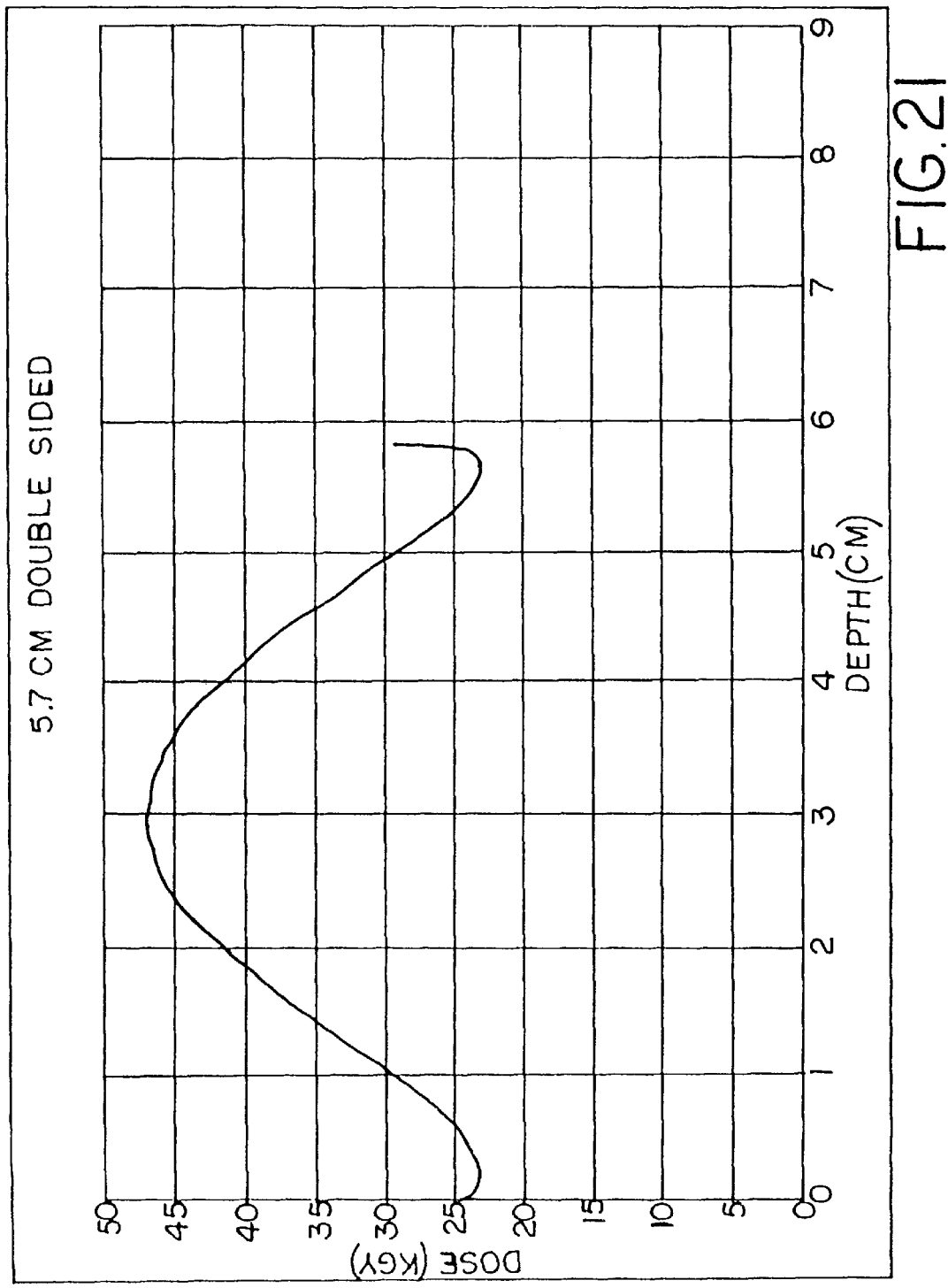
Figure 22:
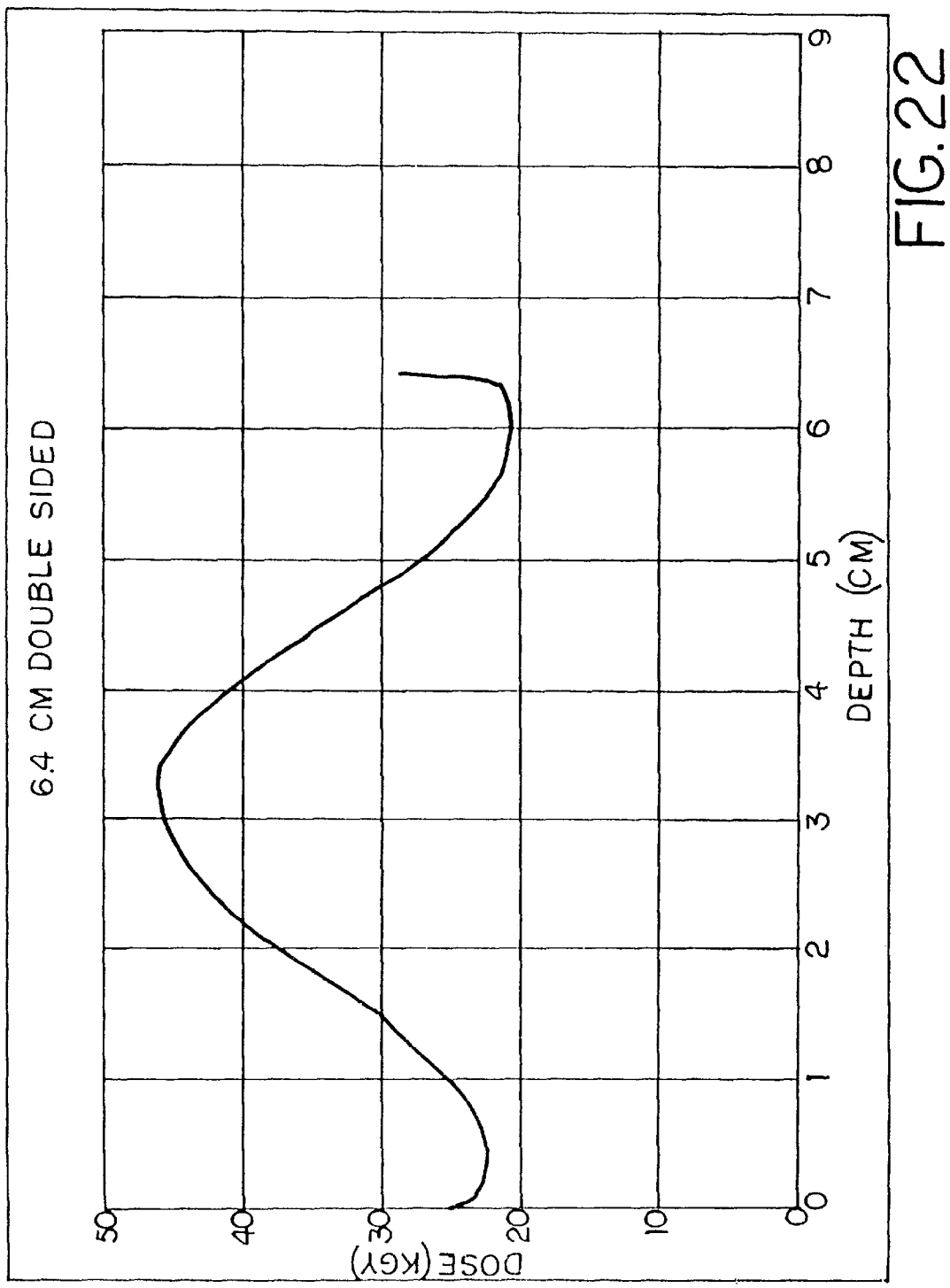
Figure 23:
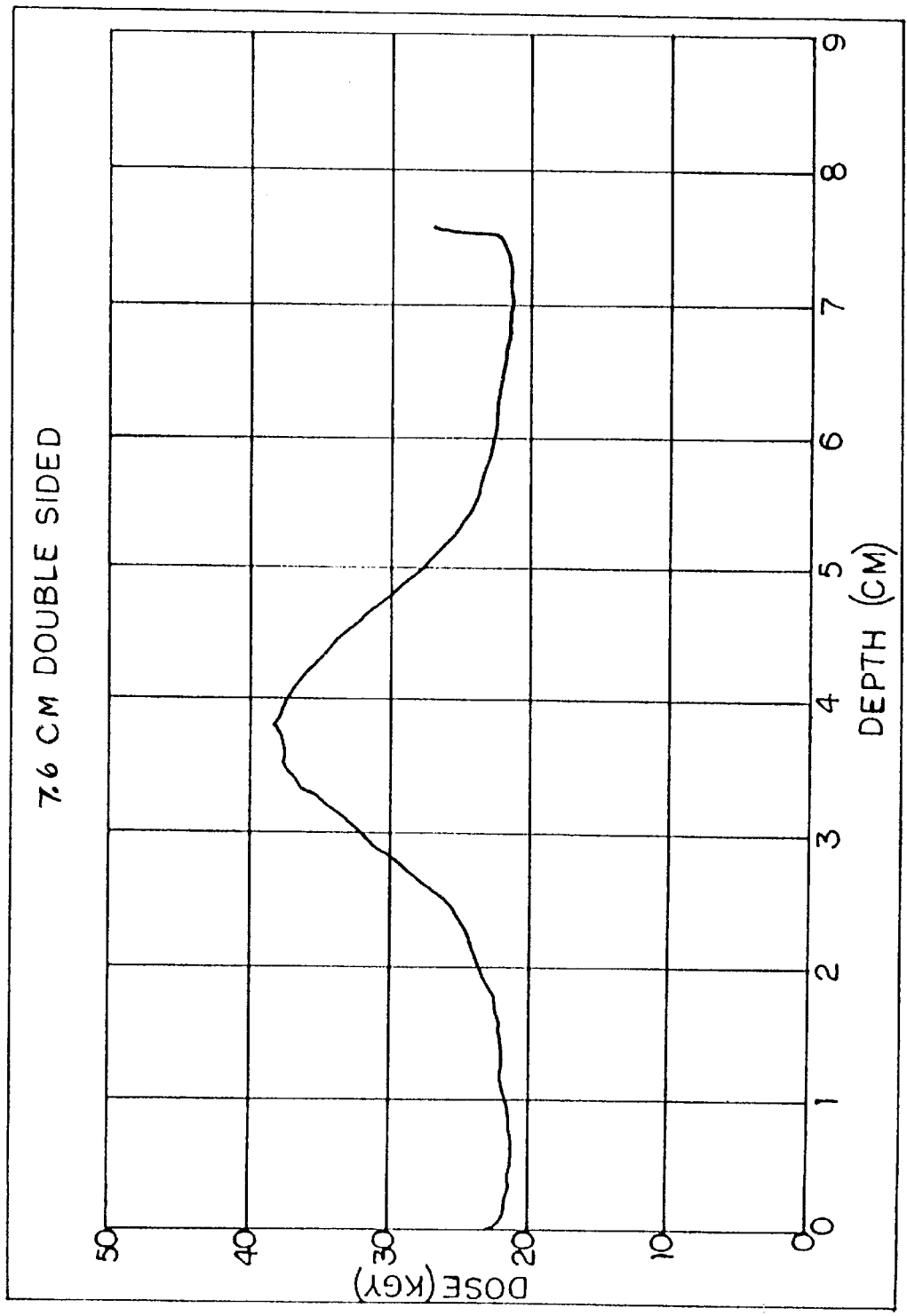
Figure 24:
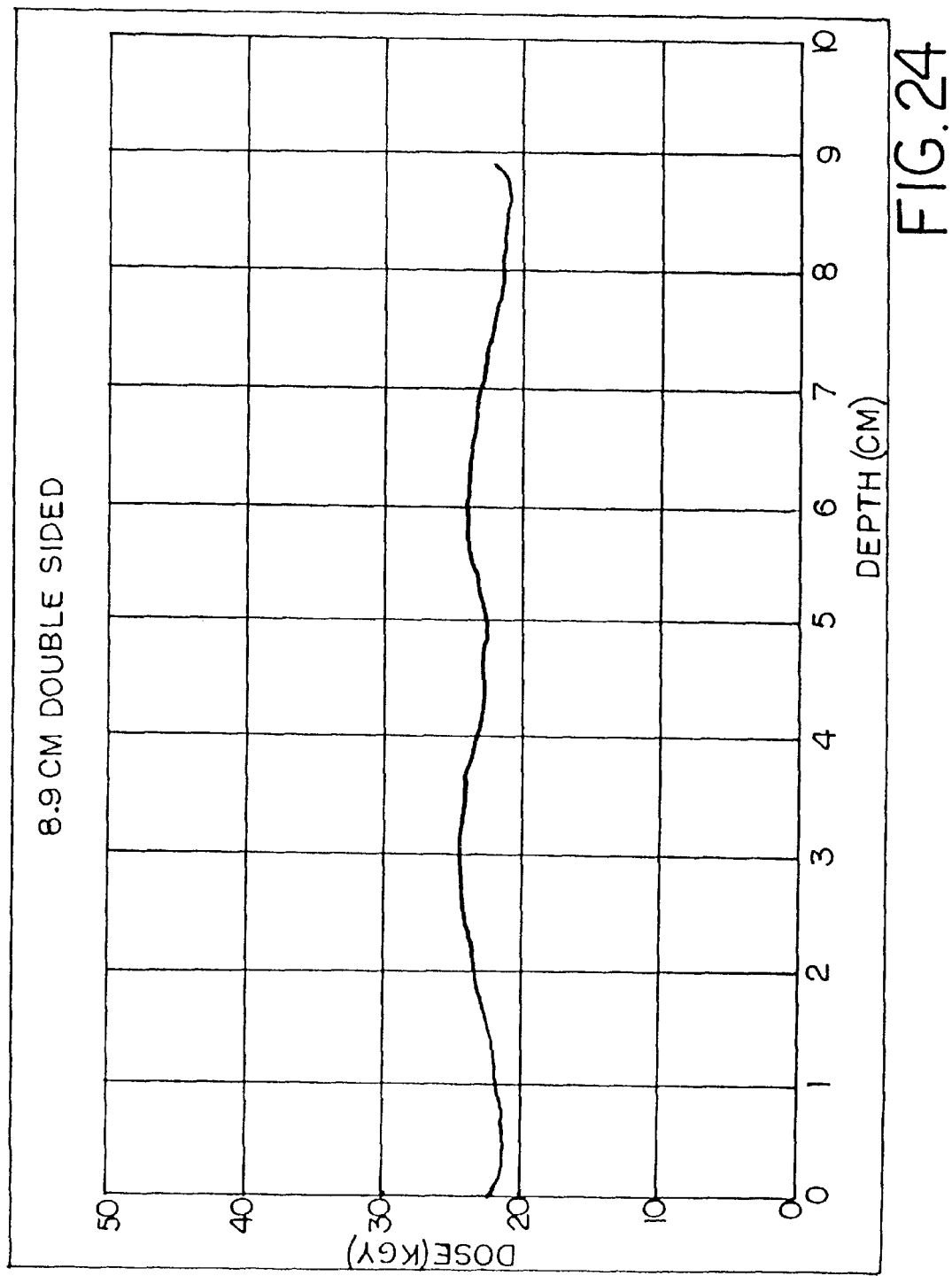
Figure 25:
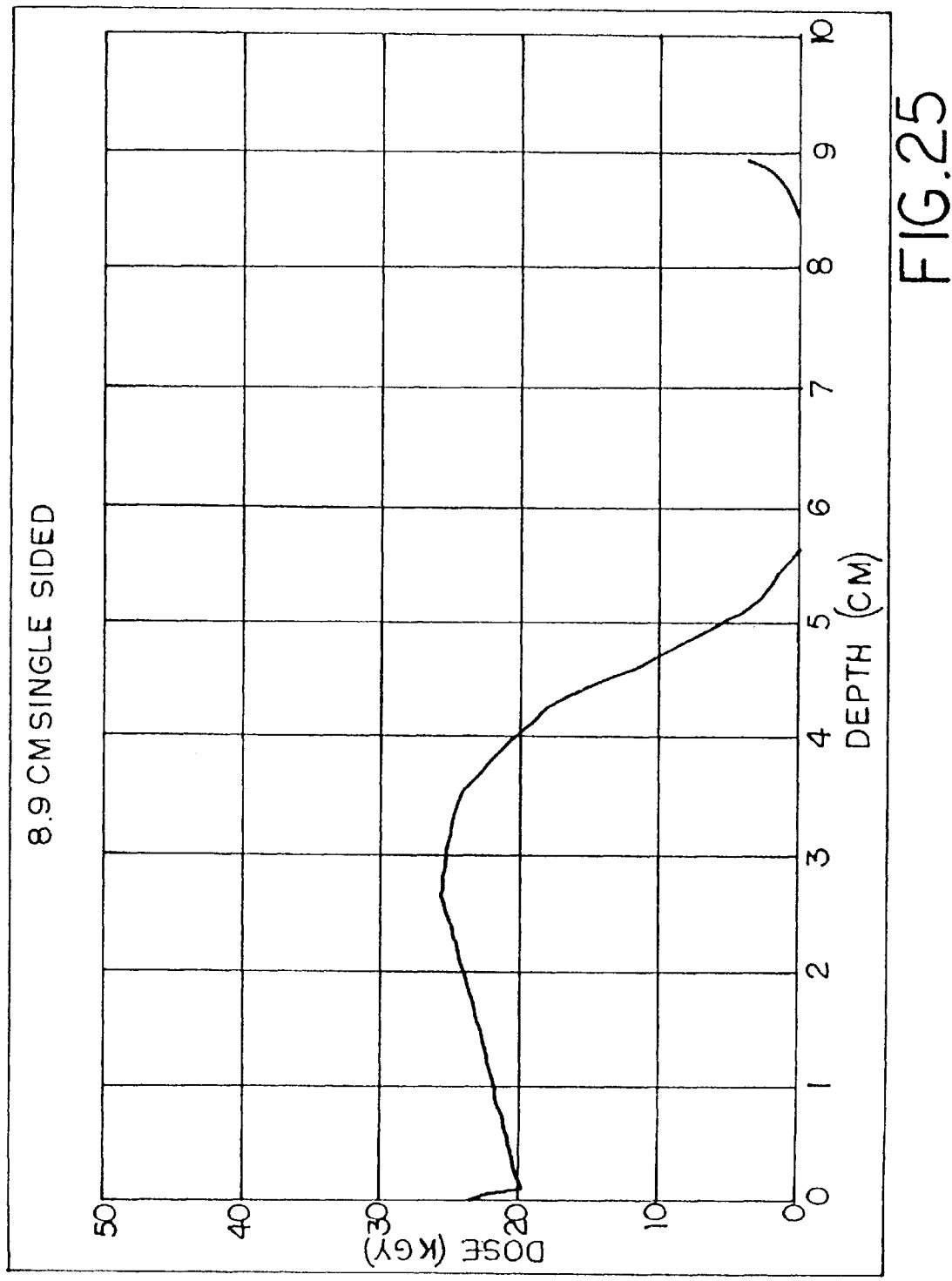
FIG. 25 is a graph of resultant dose for single-sided irradiation using a sample of the type shown in FIG. 19.

Five blocks of UHMWPE, 10 cm wide, with varying thickness were split at a 25 degree angle to form two matching wedges of material. Block thicknesses after re-assembling were 5.1, 5.7, 6.4, 7.6, and 8.9 cm. One cm wide radiochromic dosimeter film was placed down the center of the incline between the matching wedges of material as shown in FIG. 19. The wedges were then secured back in place. Each block of material was then irradiated without shielding from the top and bottom sides at 20 kGy incident dose with a 60 kW, 10 MeV electron beam. Dosimeter films were analyzed to determine the dose distribution through the thickness of the UHMWPE blocks. Results for each block are given in FIGS. 20–24. Single side irradiation dose distribution using the same technique for an 8.9 cm thick split block is shown in FIG. 25. Note that as the block thickness approaches the optimal thickness of 9.0 cm for uniform dose distribution after two sided irradiation in UHMWPE, the dose becomes uniform through the depth of the block.

Figure 26:
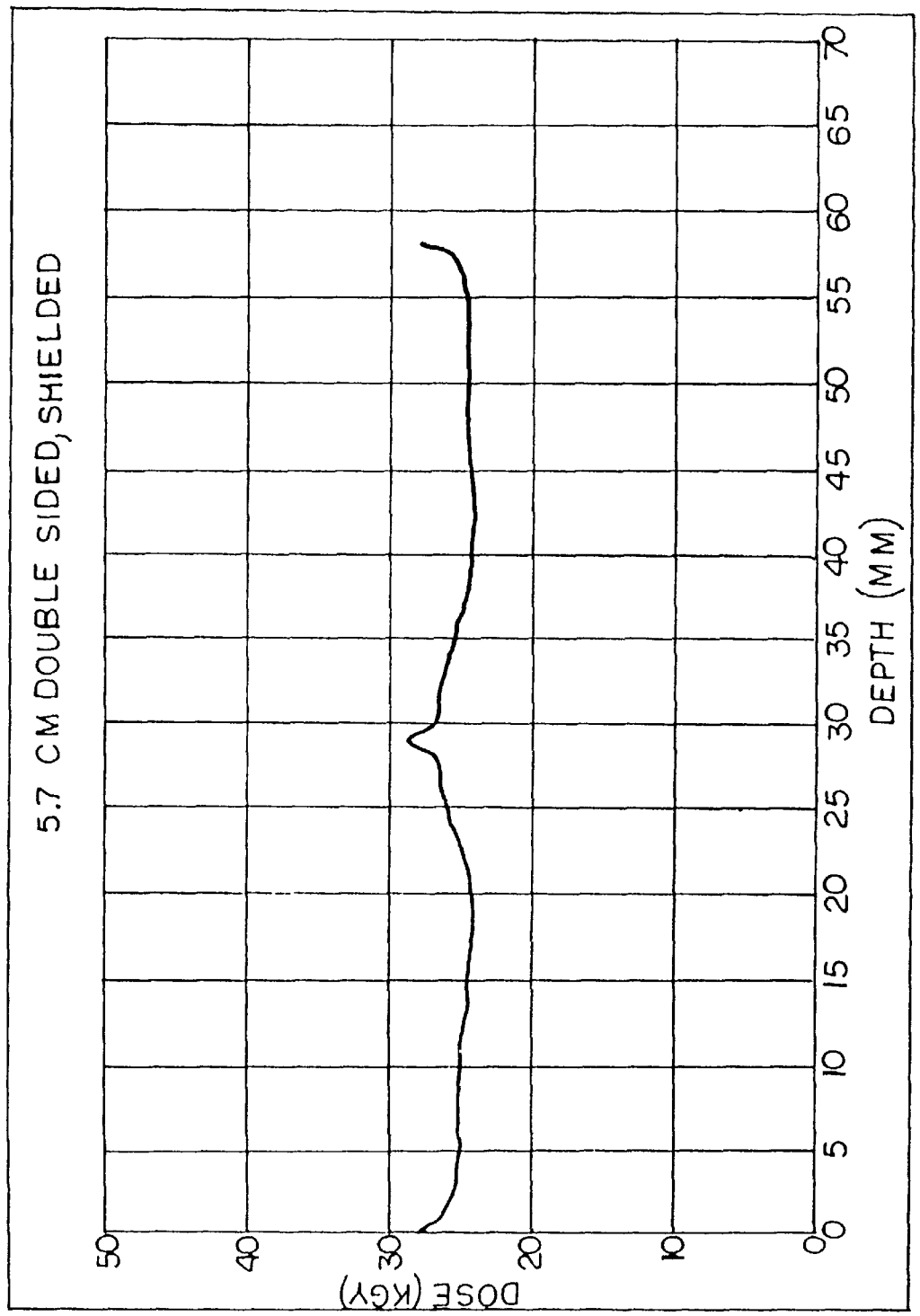
Figure 27:
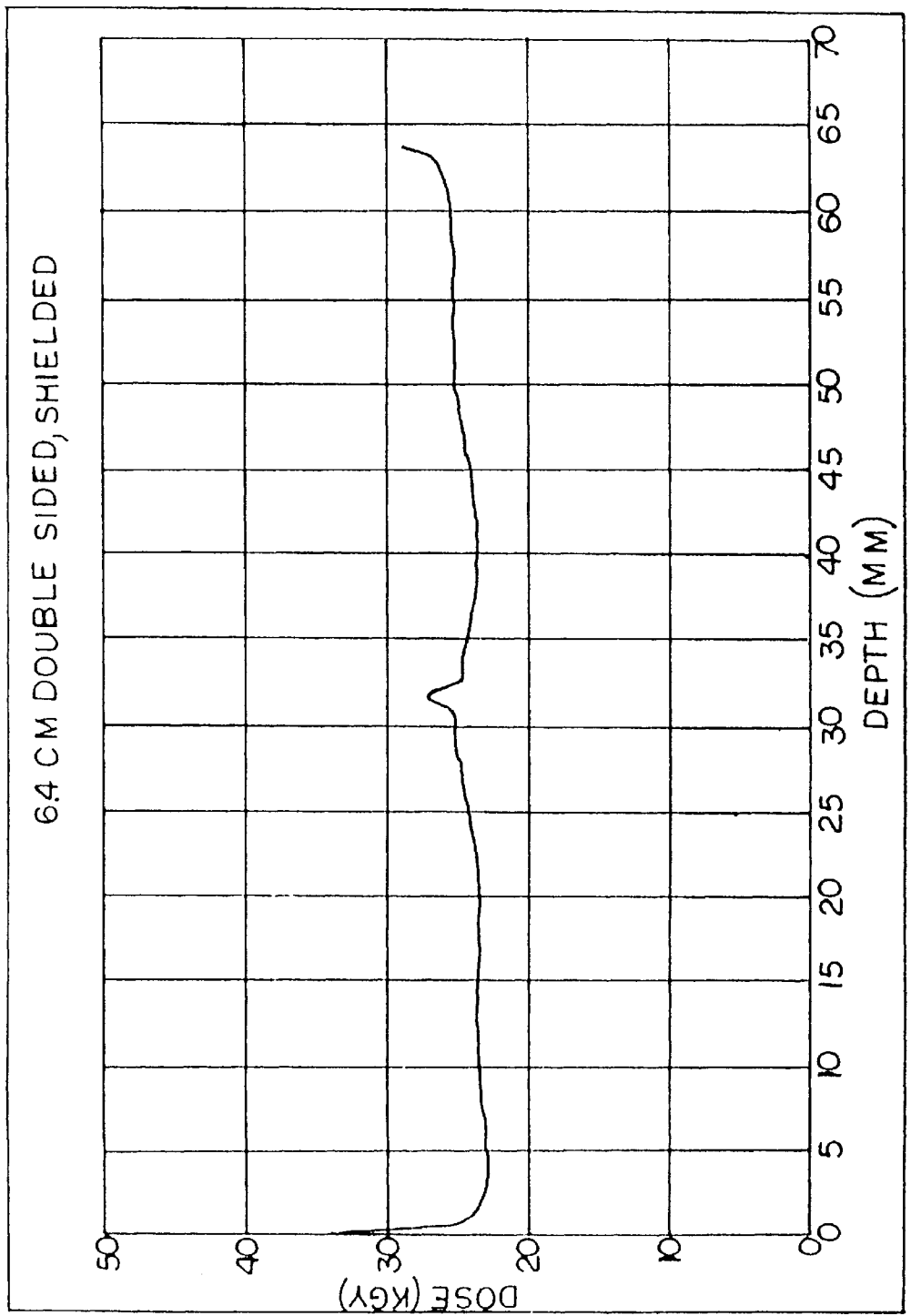

Three blocks of UHMWPE, 10 cm wide, with varying thickness were split at a 25 degree angle to form two matching wedges of material. Block thicknesses after re-assembling were 5.7, 6.4, and 7.0 cm. One cm wide radiochromic dosimeter film was placed down the center of the incline between the matching wedges of material as shown in FIG. 19. The wedges were then secured back in place. Each block of material was then irradiated with the appropriate sized shielding per formula (1), from the top and bottom sides at 20 kGy incident dose with a 60 kW, 10 MeV electron beam. One half of the shield thickness was used for each side irradiated: 0.55 cm thick aluminum plate shield for the 5.7 cm block; 0.44 cm thick aluminum plate shield for the 6.4 cm block; 0.33 cm thick aluminum plate shield for the 7.0 cm block. Dosimeter films were analyzed to determine the dose distribution through the thickness of the UHMWPE blocks. Results for each block are given in FIGS. 26–28. These results demonstrate the ability to achieve uniform doses in different thickness samples by using shielding.

A two level multi-factorial experiment was conducted to determine the effects of dose rate, shielding, moisture, and UHMWPE material size on the tendency for electrical discharge to occur during electron beam irradiation. A 60 kW, 10 MeV electron beam was used for all conditions. The UHMWPE material was machined into solid cylinders with height equal to diameter for each size. Sizes examined included 2.25 inch cylinders, 2.5 inch diameter cylinders, and 3.5 inch diameter cylinders. For the moist conditions, the pucks were placed in ordinary tap water, with the water depth less than the cylinder height. Aluminum plate shielding was used with thickness as determined per formula (1). The effects of not shielding vs. shielding was examined for the 2.25 inch diameter cylinders. Dose rates were from 50 to 100 kGy per pass until the desired final dose level for each condition was achieved. Discharge observations were by visual examination with each cylinder containing discharge given a score=1.

The data was analyzed using least squares fitting, with significance of the results determined using an F distribution of the variance ratios. Results were determined to be significant for variable effects with probability for the null hypotheses at $p \leq 0.05$. Introduction of moisture was seen to have significant effects, with moist conditions reducing discharge tendencies. Dose rate also had significant inverse effects, with increasing dose rate decreasing discharge. Effects of shielding were examined for the smallest cylinders, 2.25 inch diameter. Non-shielded cylinders discharged significantly more than shielded ones. The strongest effect was the size of cylinder, with increasing size resulting in increasing discharge.

UHMWPE block temperature effects on discharge were determined, along with effects of dose rate, moisture and block size, using a two level multi-factorial experimental design. A 60 kW, 10 MeV electron beam was used for all conditions. Block sizes were 2.25 inch square by nine inches long, and 2.75 inch square by nine inches long. Blocks were processed at ambient temperature for cold conditions, and were preheated to 60° C. overnight in an air circulating oven for the warm condition. The pre-heated blocks were transferred to the electron beam quickly so that irradiation was conducted while the block was at or near 60° C. For the cold/moist conditions, the blocks were placed in ordinary tap water adjusted to 20° C., with the water depth less than the block height. For the warm moist conditions, the tap water was pre-heated to 60° C. Aluminum plate shielding was used with thickness as determined per formula (1) for all blocks. Irradiation was from two opposite block sides, with shielding placed at the block incident face during irradiation. Dose rates were at 60 and 90 kGy per pass until the desired final dose level of 180 kGy was achieved. Discharge observations were by visual examination with each block containing discharge given a score=1, and those with no discharge a score=0.

The data was analyzed using least squares fitting, with significance of the results determined using an F distribution of the variance ratios. Results were determined to be significant for variable effects with probability for the null hypothesis at $p \leq 0.05$. Introduction of moisture was seen to have significant effects for the cold irradiation conditions, with moisture reducing discharge tendencies. Block temperature interacted with all other variables, where the warm irradiation effectively eliminated discharge for all blocks that were preheated. Dose rate had significant inverse effects for the cold irradiated blocks, with increasing dose rate decreasing discharge. Block size was significant also for the cold irradiation condition, with larger size increasing discharge tendency.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of preparing a bearing material for use in an orthopaedic implant, comprising the steps of:
   providing a radiation source;
   positioning said bearing material at a distance away from said radiation source;
   installing a shield over at least a portion of said bearing material; and
   irradiating said bearing material through said shield using said radiation source.

2. The method of claim 1 further comprising the step of forming a bearing surface on said bearing material subsequent to irradiating the bearing material.

3. The method of claim 1, wherein said shield covers a portion of said bearing material to define a shielded portion and an unshielded portion of said bearing material, and wherein said irradiating step comprises irradiating each of said shielded portion and said unshielded portion.

4. The method of claim 1, wherein said installing step occurs prior to said positioning step.

5. The method of claim 1, comprising the further step of surrounding at least a portion of said bearing material with a conductive media prior to said irradiation step.

6. The method of claim 5, wherein said surrounding step comprises submersing said bearing material in a conductive fluid.

7. The method of claim 5, wherein said conductive media comprises a metallic holder surrounding at least a portion of said bearing material.

8. The method of claim 7, comprising the further step of grounding said holder.

9. The method of claim 1, comprising the further step of submersing said bearing material in a fluid prior to said irradiation step.

10. The method of claim 9, wherein said fluid comprises at least one of an inert fluid and an electrically conductive fluid.

11. The method of claim 10, wherein said fluid comprises an inert fluid consisting of one of nitrogen and argon.

12. The method of claim 9, wherein said fluid comprises an electrically conductive fluid consisting essentially of tap water.

13. The method of claim 1, comprising the further steps of:
  repositioning said bearing material at an orientation of approximately 180° relative to a position of said bearing material after said positioning step at said distance away from said radiation source; and
  repeating said irradiating step.

14. The method of claim 1, comprising the further steps of;
  placing said bearing material on a movable conveyor; and
  conveying said bearing material past said radiation source.

15. The method of claim 14, wherein said conveying step comprises conveying said bearing material past said radiation source at a travel speed of between 20 and 80 cm/min.

16. The method of claim 15, wherein said conveying step comprises conveying said bearing material past said radiation source at a travel speed of approximately 54.2 cm/min.

17. The method of claim 1, wherein said irradiating step is carried out to impart an effective dose to said bearing material of between 30 and 300 kGy.

18. The method of claim 17, wherein said irradiating step is carried out to impart an effective dose to said bearing material of between 50 and 150 kGy.

19. The method of claim 17, wherein said irradiating step is carried out to impart an effective dose to said bearing material of between 80 and 120 kGy.

20. The method of claim 1, wherein said radiation source comprises an electron beam with an energy level of between 1 and 20 MeV at a beam power of between 1 and 120 kW during said irradiation step.

21. The method of claim 20, wherein said radiation source comprises an electron beam with an energy level of approximately 10 MeV at a beam power of approximately 60 kW during said irradiation step.

22. The method of claim 1, wherein said shield has a substantially constant thickness in a direction toward said radiation source.

23. The method of claim 1, wherein said shield includes a cutout.

24. The method of claim 1, wherein said shield includes a thicker portion.

25. The method of claim 1, wherein said shield has a density which is approximately the same as said bearing material.

26. The method of claim 25, wherein said shield and said bearing material are comprised of a same material.

27. The method of claim 26, wherein said shield and said bearing material are each comprised of a polymer.

28. The method of claim 27, wherein said shield and said bearing material are each comprised of ultra-high-molecular-weight polyethylene.

29. The method of claim 1, wherein said shield has a thickness extending toward said radiation source which is determined by the mathematical equation:

$$\text{Total Shield Thickness} = \frac{(\text{optimum sample thickness} - \text{sample thickness}) \times (\text{sample material density})}{(\text{shield material density})}$$

30. The method of claim 1 further comprising the step of preheating the bearing material to between 20 and 60° C. before irradiating it.

31. The method of claim 30 wherein the bearing material is preheated to between 40 and 50° C. before irradiating it.

32. A method of preparing a bearing material for use in an orthopaedic implant, comprising the steps of:
  providing a radiation source;
  positioning said bearing material on a conveyor at a distance away from said radiation source;
  installing a shield over at least a portion of said bearing material;
  conveying said bearing material past said radiation source at a travel speed of between 20 and 80 cm/min; and
  irradiating said bearing material through said shield using said radiation source with an effective dose of between 80 and 120 kGy.

33. The method of claim 32 further comprising the step of forming a bearing surface on said bearing material subsequent to irradiating the bearing material.

34. A method of preparing a bearing material for use in an orthopaedic implant, comprising the steps of:
  providing a radiation source;
  positioning said bearing material at a distance away from said radiation source;
  electrically grounding said bearing material; and
  irradiating said bearing material using said radiation source.

35. The method of claim 34 further comprising the step of forming a bearing surface on said bearing material subsequent to irradiating the bearing material.

36. The method of claim 34, comprising the further step of installing a shield over at least a portion of said bearing material.

37. The method of claim 1 wherein the bearing material has a non-rectangular cross section and the shield has an at least partially corresponding non-rectangular cross section.

* * * * *